US 11,084,897 B2

(12) United States Patent
Hedrick et al.

(10) Patent No.: US 11,084,897 B2
(45) Date of Patent: Aug. 10, 2021

(54) CHEMICAL COMPOUNDS WITH PERFLUOROARYL GROUPS THAT CAN FACILITATE POST-SYNTHESIS FUNCTIONALIZATION

(71) Applicant: International Business Machines Corporation, Armonk, NY (US)

(72) Inventors: James L. Hedrick, Pleasanton, CA (US); Nathaniel H. Park, San Jose, CA (US); Gavin Jones, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 192 days.

(21) Appl. No.: 15/839,420

(22) Filed: Dec. 12, 2017

(65) Prior Publication Data

US 2019/0177466 A1  Jun. 13, 2019

(51) Int. Cl.

| *C08G 18/32* | (2006.01) |
| *C08G 18/83* | (2006.01) |
| *C08G 18/28* | (2006.01) |
| *C08K 5/37* | (2006.01) |
| *C08G 18/75* | (2006.01) |

(Continued)

(52) U.S. Cl.
CPC ....... *C08G 18/329* (2013.01); *C08G 18/2885* (2013.01); *C08G 18/3275* (2013.01); *C08G 18/3812* (2013.01); *C08G 18/75* (2013.01); *C08G 18/755* (2013.01); *C08G 18/837* (2013.01); *C08G 63/00* (2013.01); *C08G 64/165* (2013.01); *C08G 64/1633* (2013.01); *C08G 64/18* (2013.01); *C08G 64/42* (2013.01);

(Continued)

(58) Field of Classification Search
CPC .............. C08G 18/329; C08G 18/2885; C08G 18/3275; C08G 18/75; C08G 18/3812; C08G 18/755; C08G 63/00; C08G 64/1633; C08G 64/165; C08G 64/18; C08G 81/00
See application file for complete search history.

(56) References Cited

U.S. PATENT DOCUMENTS

| 3,320,335 A | 5/1967 | Hedrick et al. |
| 3,558,568 A | 1/1971 | Kobayashi et al. |

(Continued)

FOREIGN PATENT DOCUMENTS

| JP | 63287948 A | * 11/1988 | ........... G03F 7/0233 |
| WO | WO-9428054 | * 12/1994 | ............. C08G 77/42 |

(Continued)

OTHER PUBLICATIONS

JP-63287948_Nov. 1988_English Translation.*

(Continued)

*Primary Examiner* — Michael L Leonard
(74) *Attorney, Agent, or Firm* — Amin, Turocy & Watson, LLP

(57) ABSTRACT

Techniques regarding chemical compounds comprising perfluoroaryl groups that can facilitate post-synthesis functionalization are provided. For example, one or more embodiments described herein can comprise a chemical compound. The chemical compound can comprise a molecular backbone. The chemical compound can also comprise a pendent functional group bonded to the molecular backbone. The pendent functional group can comprise a perfluoroaryl group and a methylene group.

17 Claims, 15 Drawing Sheets

(51) Int. Cl.
| | |
|---|---|
| *C08G 64/42* | (2006.01) |
| *C08J 7/12* | (2006.01) |
| *C08K 5/5419* | (2006.01) |
| *C08G 81/00* | (2006.01) |
| *C08G 63/00* | (2006.01) |
| *C08G 64/16* | (2006.01) |
| *C08G 64/18* | (2006.01) |
| *C08G 18/38* | (2006.01) |

(52) U.S. Cl.
CPC ............... *C08G 81/00* (2013.01); *C08J 7/12* (2013.01); *C08K 5/37* (2013.01); *C08K 5/5419* (2013.01)

(56) References Cited

U.S. PATENT DOCUMENTS

| | | | | |
|---|---|---|---|---|
| 4,349,658 | A | * | 9/1982 | Mark .................. C08G 63/682 525/439 |
| 4,508,916 | A | * | 4/1985 | Newell .............. C08G 18/5003 522/96 |
| 8,044,194 | B2 | | 10/2011 | Dubois et al. |
| 8,236,902 | B2 | | 8/2012 | Hogen-Esch et al. |
| 8,440,176 | B2 | | 5/2013 | Laronde et al. |
| 8,829,128 | B2 | | 9/2014 | Huhtanen et al. |
| 9,006,337 | B2 | | 4/2015 | Zhong et al. |
| 9,108,172 | B2 | | 8/2015 | Mattmann et al. |
| 9,389,183 | B2 | | 7/2016 | Chen et al. |
| 2010/0228060 | A1 | | 9/2010 | Langstrom et al. |
| 2010/0305281 | A1 | * | 12/2010 | Fujiwara ............ C08G 64/0241 525/461 |
| 2011/0207887 | A1 | | 8/2011 | Duc et al. |
| 2012/0062228 | A1 | | 3/2012 | Williamson et al. |
| 2013/0079465 | A1 | | 3/2013 | Desbois et al. |
| 2013/0102728 | A1 | | 4/2013 | Yang et al. |
| 2016/0289399 | A1 | | 10/2016 | Underwood et al. |
| 2017/0240668 | A1 | | 8/2017 | Coatex |
| 2017/0291971 | A1 | * | 10/2017 | Serrano ................ C08F 220/60 |
| 2019/0177466 | A1 | | 6/2019 | Hedrick et al. |

FOREIGN PATENT DOCUMENTS

| | | | |
|---|---|---|---|
| WO | 2009009251 A1 | 1/2009 | |
| WO | 2016049123 A1 | 3/2016 | |
| WO | WO-2016037630 A1 * | 3/2016 | ............... C08F 8/40 |
| WO | 2016200956 A1 | 12/2016 | |

OTHER PUBLICATIONS

STN Search of CAS No. 21634-97-9_Entered Nov. 16, 1984.*
Lee et al., Injectable biodegradable hydrogels from vitamin D-functionalized polycarbonates for the delivery of avastin with enhanced therapeutic efficiency against metastatic colorectal cancer, Biomacromolecules, 2015, pp. 465-475, vol. 16.
Nederberg et al., Biodegradable nanostructures with selective lysis of microbial membranes, Nature Chemistry, May 2011, pp. 409-414, vol. 3.
Ono et al., Benzyl chloride-functionalized polycarbonates: a versatile platform for the synthesis of functional biodegradable polycarbonates, Macromolecules, 2014, pp. 7725-7731, vol. 47.
Park et al., Expanding the cationic polycarbonate platform: attachment of sulfonium moieties by postpolymerization ring opening of epoxides, ACS Macro Letters, 2016, pp. 1247-1252, vol. 5.
Chan et al., Chemically modifiable N-heterocycle-functionalized polycarbonates as a platform for diverse smart biomimetic nanomaterials, Chemical Science, 2014, pp. 3294-3300, vol. 5.
Isik et al.,Tuning the Selectivity of Biodegradable Antimicrobial Cationic Polycarbonates by Exchanging the Counter-Anion, Macromolecular Bioscience, 2016, 8 Pages.
Kubo et al., Multifunctional homopolymers: postpolymerization modification via sequential nucleophilic aromatic substitution, Macromolecules, 2016, 8 Pages.
Spokoyny et al., A perfluoroaryl-cysteine S(N)Ar chemistry approach to unprotected peptide stapling, Journal of the American Chemical Society, 2013, pp. 5946-5949, vol. 135.
Park et al., Organocatalyzed synthesis of poly(aryl thioethers), Nature Communications, Last Accessed Oct. 31, 2017, 7 Pages, vol. 8, Issue 166.
Pratt et al., Exploration, optimization, and application of supramolecular thiourea-amine catalysts for the synthesis of lactide (co)polymers, Macromolecules, 2006, pp. 7863-7871, vol. 39.
Quast et al., Hyperbranched Polyfluorinated benzyl ether polymers: Mechanism, kinetics, and optimization, Journal of Polymer Science Part A: Polymer Chemistry, 2014, pp. 985-994, vol. 52.
Hall, Synthesis, Characterization, and Polymerization of Sulfonamide Based Bifunctional Monomers, 2016, 83 pages.
Liu, Yaya, et al. "A Switch from Anionic to Bifunctional H-Bonding Catalyzed Ring-Opening Polymerizations Towards Polyether—Polyester Diblock Copolymers." Polymer Chemistry 9.2 (2018): 154-159. Polymer Chemistry (RSC Publishing). 4 pages.
Hu, Xin, et al. "Continuous Flow Ring-Opening Polymerizations." Reaction Chemistry & Engineering 2.1 (2017): 20-26. Reaction Chemistry & Engineering (RSC Publishing). 18 pages.
Lin, Binhong, et al. "Organic Ring-Opening Polymerization Catalysts: Reactivity Control by Balancing Acidity." Macromolecules, 2018, 51 (8), pp. 2932-2938. 7 pages.
Lin, Binhong, et al. "Urea Anions: Simple, Fast, and Selective Catalysts for Ring-Opening Polymerizations." J. Am. Chem. Soc., 2017, 139 (4), pp. 1645-1652. 8 pages.
Van Den Berg, Sebastiaan, et al. "Clickable Polylactic Acids by Fast Organocatalytic Ring-Opening Polymerization in Continuous Flow." Macromolecules, 2016. 9 pages.
Melker, Anna, et al. "Continuous Flow Synthesis of Poly(Methyl Methacrylate) via a Light-Mediated Controlled Radical Polymerization." Journal of Polymer Science Polymer Chemistry. 2015, 53, 2693-2698. 6 pages.
Gutmann, Bernhard, et al. "Continuous-Flow Technology—A Tool for the Safe Manufacturing of Active Pharmaceutical Ingredients." Angew. Chem. Int. Ed. 2015, 54, 6688-6728. 41 pages.
Britton, Joshua, et al. "Multi-Step Continuous-Flow Synthesis." Chem. Soc. Rev. 2017, 46, 1250-1271. 22 pages.
Zhang, Xiangyi, et al. "Fast and selective ring-opening polymerizations by alkoxides and thioureas". Nat. Chem. 2016, 8, 1047-1053. 7 pages.
Kamber, Nahrain, et al. "Organocatalytic Ring-Opening Polymerization." Chem. Rev. 2007, 107, 5813-5840. 28 pages.
Zhu, Ning, et al. "Enzymatic Continuous Flow Synthesis of Thiol-Terminated Poly(□-Valerolactone) and Block Copolymers." Macromolecular Rapid Communications 2018. 6 pages.
Zhu, Ning, et al. "Sn(OTf)2 Catalyzed Continuous Flow Ring-Opening Polymerization of ε-Caprolactone." RSC Advances, 2015, 5, 31554-31557. 4 pages.
Zhu, Ning, et al. "Continuous Flow Protecting-Group-Free Synthetic Approach to Thiol-Terminated Poly(ε-Caprolactone)." European Polymer Journal 2016, 80, 234-239. 6 pages.
Kundu Santanu, et al. "Continuous Flow Enzyme-Catalyzed Polymerization in a Microreactor." Journal of the American Chemical Society. 2011, 133, 6006-6011. 13 pages.
Reis, Marcus H., et al. "Continuous-Flow Chemistry for the Determination of Comonomer Reactivity Ratios." Polymer Chemistry. Jan. 2018. 7 pages.
Abe, Akihiro, et al. "Controlled Polymerization and Polymeric Structures: Flow Microreactor Polymerization, Micelles Kinetics, Polypeptide Ordering, Light Emitting Nanostructures." Advances in Polymer Science 259. 2013. 253 pages.
Leibfarth, Frank A., et al. "Scalable Synthesis of Sequence-Defined, Unimolecular Macromolecules by Flow-IEG." PNAS 2015, 201508599. 6 pages.
Zhu, Ning, et al. "Organocatalyzed Continuous Flow Ring-Opening Polymerizations to Homo- and Block-Polylactones." Polymer 2016, 84, 391-397. 7 pages.
Porta, Riccardo, et al. "Flow Chemistry: Recent Developments in the Synthesis of Pharmaceutical Products." Organic. Process Research & Development. Nov. 2015. 67 pages.

(56) References Cited

OTHER PUBLICATIONS

Chen, Mao, et al. "Improving Photo-Controlled Living Radical Polymerization from Trithiocarbonates through the Use of Continuous-Flow Techniques." Chem. Commun. 2015, 51, 6742-6745. 6 pages.
Micic, Nenad, et al. "Scale-up of the Reversible Addition-Fragmentation Chain Transfer (RAFT) Polymerization Using Continuous Flow Processing." Processes 2014, 2, 58-70. 13 pages.
Peng, J., et al. "The in Situ Formation of Nanoparticles via RAFT Polymerization-Induced Self-Assembly in a Continuous Tubular Reactor." Polymer Chemistry 2017, 8, 1495-1506. 14 pages.
Deihl, Christina, et al. "Accelerated Continuous Flow RAFT Polymerization." Macromolecules 2010, 43, 10311-10314. 4 pages.
Ramsey, Bonnie, L., et al. "Photoinduced Organocatalyzed Atom Transfer Radical Polymerization Using Continuous Flow." Macromolecules 2017, 50, 2668-2674. 7 pages.
Parida, Dambarudhar, et al. "Coil Flow Inversion as a Route to Control Polymerization in Microreactors." Macromolecules 2014, 47, 3282-3287. 6 pages.
Morsbach, Jan, et al. "Living Polymer Chains with Predictable Molecular Weight and Dispersity via Carbanionic Polymerization in Continuous Flow: Mixing Rate as a Key Parameter." Macromolecules 2016, 49, 5043-5050. 8 pages.
Mastan, Erlita, et al. "Continuous Production of Multiblock Copolymers in a Loop Reactor: When Living Polymerization Meets Flow Chemistry." Macromolecules 2017. 15 pages.
Natalello, Adrian, et al. "Living Anionic Polymerization in Continuous Flow: Facilitated Synthesis of High-Molecular Weight Poly(2-Vinylpyridine) and Polystyrene." Organic Process Research & Development. Jul. 2014. 7 pages.
Nagaki, Aiichiro "Microflow-System-Controlled Anionic Polymerization of Styrenes." Macromolecules 2008, 41, 6322-6330. 9 pages.
Tonhauser, Christoph, et al. "Microflow Technology in Polymer Synthesis." Macromolecules 2012, 45, 9551-9570. 20 pages.
Mascia, Salvatore, et al. "End-to-End Continuous Manufacturing of Pharmaceuticals: Integrated Synthesis, Purification, and Final Dosage Formation." Angew. Chem. Int. Ed. 2013, 52, 12359-12363. 6 pages.
Adamo, Andrea, et al. "On-Demand Continuous-Flow Production of Pharmaceuticals in a Compact, Reconfigurable System." Science 2016, 352, 61-67. 8 pages.
International Search Report and Written Opinion received for PCT Application Serial No. PCT/IB2018/059556, dated Mar. 20, 2019, 9 pages.
Mell, Peter, et al. "The NIST Definition of Cloud Computing." National Institute of Standards and Technology. Sep. 2011. 7 pages.
Lui, et al. "A switch from anionic to bifunctional H-bonding catalyzed ring-opening polymerizations towards polyether-polyester diblock copolymers." Polym. Chem., 2018, 9, 154-159. 6 pages.
Non-Final Office Action received for U.S. Appl. No. 16/028,919 dated Feb. 14, 2020, 32 pages.
Notice of Allowance received for U.S. Appl. No. 16/029,025 dated Feb. 6, 2020, 56 pages.
Non-Final Office Action received for U.S. Appl. No. 16/028,989 dated Mar. 30, 2020, 109 pages.
Final Office Action received for U.S. Appl. No. 16/028,989 dated Aug. 25, 2020, 119 pages.
Whitmarsh (Synthesis and Chemical Modification of Polyoxyalkylene Block Copolymers; in Nonionic Surfactants Polyoxyalkylene Block copolymers, edited by Vaughn Nace, Marcel Dekker, 1996, Chapter 1, excerpt pp. 1-4). (Year: 1996).
Hassouna et al., "Phosphazene/triisobutylaluminum-promoted anionic ring-opening polymerization of 1,2-epoxybutane initiated by secondary carbamates", Polymer Chemistry, vol. 8, 2017, pp. 4005-4013.
Hu et al., "Ring-Opening Alternating Copolymerization of Epoxides and Dihydrocoumarin Catalyzed by a Phosphazene Superbase", Macromolecules, vol. 49, 2016, pp. 4462-4472.
Final Office Action received for U.S. Appl. No. 16/028,919 dated Apr. 9, 2020, 16 pages.

* cited by examiner

| Polycarbonate Sample | Initiator | Catalyst | [I]:[M] | Time | Conversion | Dp | $M_n$ (NMR) | $M_n$ (GPC) | Ð (GPC) |
|---|---|---|---|---|---|---|---|---|---|
| First | mPEG$_{5k}$-OH | TfOH (10 mol%) | 1:10 | 48 hours | 78% | 7.3 | 7475 | 12693 | 1.06 |
| Second | mPEG$_{5k}$-OH | DBU, TU (5 mol%) | 1:10 | 15 minutes | 96% | 10 | 8400 | 11563 | 1.07 |
| Third | mPEG$_{5k}$-OH | TU-A (5 mol%) | 1:10 | 10 minutes | 94% | 7.4 | 7509 | 12679 | 1.08 |
| Fourth | BnOH | DBU, TU (5 mol%) | 1:25 | 20 minutes | 92% | 30 | 10200 | 7721 | 1.16 |
| Fifth | HO-mPEG$_{10k}$-OH | DBU, TU (5 mol%) | 1:10 | 20 minutes | 97% | 4.4 | 12992 | 22467 | 1.11 |
| Sixth | mPEG$_{5k}$-OH | DBU, TU (5 mol%) | 1:5:5 | 15 minutes | 96% | 9.7 | 8310 | 10258 | 1.07 |
| Seventh | mPEG$_{5k}$-OH | DBU, TU (5 mol%) | 1:1:9 | 15 minutes | 96% | 9.9 | 8389 | 10403 | 1.06 |

FIG. 5

CHEMICAL COMPOUNDS WITH PERFLUOROARYL GROUPS THAT CAN FACILITATE POST-SYNTHESIS FUNCTIONALIZATION

BACKGROUND

The embodiments relate to one or more chemical compounds comprising perfluoroaryl groups, and more specifically, to one or more chemical compounds containing perfluoroaryl groups that can be functionalized post-synthesis of the one or more chemical compounds.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods and/or compositions regarding chemical compounds with perfluoroaryl groups are described.

According to an embodiment, a chemical compound is provided. The chemical compound can comprise a molecular backbone. The chemical compound can also comprise a pendent functional group bonded to the molecular backbone. The pendent functional group can comprise a perfluoroaryl group and a methylene group.

According to another embodiment, a polymer is provided. The polymer can comprise a molecular backbone comprising a polycarbonate structure. The polymer can also comprise a pendent functional group covalently bonded to the molecular backbone. The pendent functional group can comprise a perfluoroaryl group and a methylene group.

According to another embodiment, polymer is provided. The polymer can comprise a molecular backbone comprising a polyurethane structure. The polymer can also comprise a pendent functional group covalently bonded to the molecular backbone. The pendent functional group can comprise a perfluoroaryl group and a methylene group.

According to an embodiment, a method is provided. The method can comprise functionalizing a chemical compound by covalently bonding a trimethylsilyl protected thiol to a pendent functional group of the chemical compound in a presence of a catalyst. The pendent functional group can comprise a perfluoroaryl group and a methylene group.

According to an embodiment, a method is provided. The method can comprise functionalizing a chemical compound by covalently bonding a trimethylsilyl protected thiol to a pendent perfluoroaryl group of the chemical compound. The chemical compound can comprise a molecular backbone. Also, the molecular backbone can comprise the pendent perfluoroaryl group bonded to an electron-withdrawing structure.

BRIEF DESCRIPTION OF THE DRAWINGS

FIG. 5 illustrates a diagram of an example, non-limiting chart that can depict structural characteristics of one or more polymers in accordance with one or more embodiments described herein.

DETAILED DESCRIPTION

Figure 1:
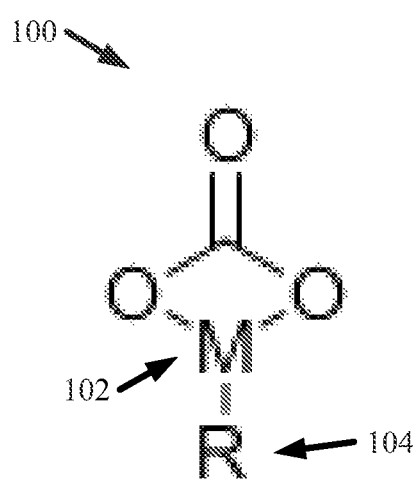
FIG. 1 illustrates a diagram of an example, non-limiting chemical structure that can characterize one or more monomers in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

The post-synthesis modification of polycarbonates can be important for the development of functional materials for therapeutic applications. With the appropriate choice of pendant functional groups, polycarbonates can be readily diversified into a myriad of biomedical applications ranging from injectable hydrogels for therapeutic delivery to antimicrobial polymers with high efficacy. Unfortunately, not all functional groups are compatible with the ring-opening polymerization process used to prepare polycarbonates. Additionally, de novo monomer synthesis can be synthetically tedious, making scale up a challenging endeavor. Thus, in order to enable a broader diversity of functional groups to be incorporated into polycarbonate platforms, one or more handles for further functionalization of polycarbonate scaffolds have been utilized. These handles have been extensively utilized for the incorporation of additional functional groups in a synthetically convergent manner, facilitating a diverse array of biomedical applications.

However, in some cases, extended reaction times, elevated temperatures, or use of stoichiometric amounts of base are required to achieve high degrees of functionalization of the polycarbonate backbone. While effective, these conditions have the potential to compromise the backbone integrity and broaden the molecular weight distribution— particularly when more basic reagents are used. Additionally, some instances of post-synthesis modification of polycarbonates involves the use of azide-alkyne click chemistry. While effective, the use of hazardous azide reagents and problem of residual copper retained in the polymer matrix render this approach less desirable for the preparation of materials for therapeutic applications.

One approach to post-synthesis modification can involve the use of nucleophilic aromatic substitution ($S_NAr$) on a highly activated aryl electrophile. $S_NAr$ reactions have the advantage of being compatible with an array of functional groups and nucleophiles, depending on the reaction conditions utilized. Unfortunately, standard reaction conditions for $S_NAr$ usually require excess base, elevated temperature, extended reaction times, and produces a stoichiometric salt byproduct, which can necessitate removal in subsequent purification steps. As such, the typical conditions for $S_NAr$ could be incompatible with the more sensitive polycarbonate backbones.

Various embodiments described herein can regard one or more conditions that can enable catalytic $S_NAr$ under mild reaction conditions. For example, one or more chemical compounds (e.g., monomers and/or polymers), schemes, and/or method described herein can regard the use of perfluoroaryls in combination with thiols ("SuFex reactions"). SuFex reactions can be utilized in a number of different applications including peptide stapling and post-synthesis modification of polymers. In order to overcome the requisite need for stoichiometric base, catalytic conditions for the one or more SuFex reactions described herein can rely on the use of trimethylsilyl protected thiols. The modification rendered by the one or more SuFex reactions described herein can exhibit a dramatic increase of reactivity and be amenable for producing new condensation polymers that can be easily purified as the primary byproduct is a gas. Thus, one or more embodiments described herein can comprise post-synthesis functionalization of polycarbonate scaffolds with minimal degradation of backbone while giving a high degree of control over polymer functionalization.

FIG. 1 illustrates a diagram of an example, non-limiting chemical formula 100 that can characterize one or more cyclic monomers that can be used to create one or more perfluoroaryl polycarbonates. Repetitive description of like elements employed in other embodiments described herein is omitted for sake of brevity.

As shown in FIG. 1, one or more cyclic monomers that can be characterized by chemical formula 100 can comprise one or more carbonate groups. The one or more carbonate groups can be covalently bonded to a molecular backbone 102. The "M" shown in FIG. 1 can represent the molecular backbone 102. The molecular backbone 102 can be a central chain of covalently bonded atoms that form the primary structure of the one or more cyclic monomers that can be characterized by chemical formula 100. In various embodiments described herein, the one or more cyclic monomers that can be characterized by chemical formula 100 can comprise side chains formed by bonding one or more functional groups to the molecular backbone 102.

The molecular backbone 102 can comprise a plurality of covalently bonded atoms. The plurality of atoms can be bonded in any desirable formation, including, but not limited to: chain formations, ring formations, and/or a combination thereof. The molecular backbone 102 can comprise one or more chemical structures including, but not limited to: alkyl structures, aryl structures, alkenyl structures, aldehyde structures, ester structures, carboxyl structures, carbonyl structures, amine structures, amide structures, phosphide structures, phosphine structures, a combination thereof, and/or the like. One of ordinary skill in the art will recognize that the number of atoms that can comprise the molecular backbone 102 can vary depending of the desired function of the one or more cyclic monomers.

The one or more cyclic monomers that can be characterized by chemical formula 100 can also comprise one or more pendent functional groups 104. As shown in FIG. 1, the "R" can represent one or more pendent functional groups 104. The one or more pendent functional groups 104 can be covalently bonded to the molecular backbone 102. Further, the one or more pendent functional groups 104 can comprise one or more perfluoroaryl groups and/or one or more methylene groups. For example, one or more methylene groups can serve to link the one or more perfluoroaryl groups to the molecular backbone 102. The one or more perfluoroaryl groups can comprise one or more aryls with a various number of ring members ranging from greater than or equal to four ring members and less than or equal to 10 ring members. For example, the one or more pendent functional groups 104 can be perfluorobenzyl groups.

Figure 2:
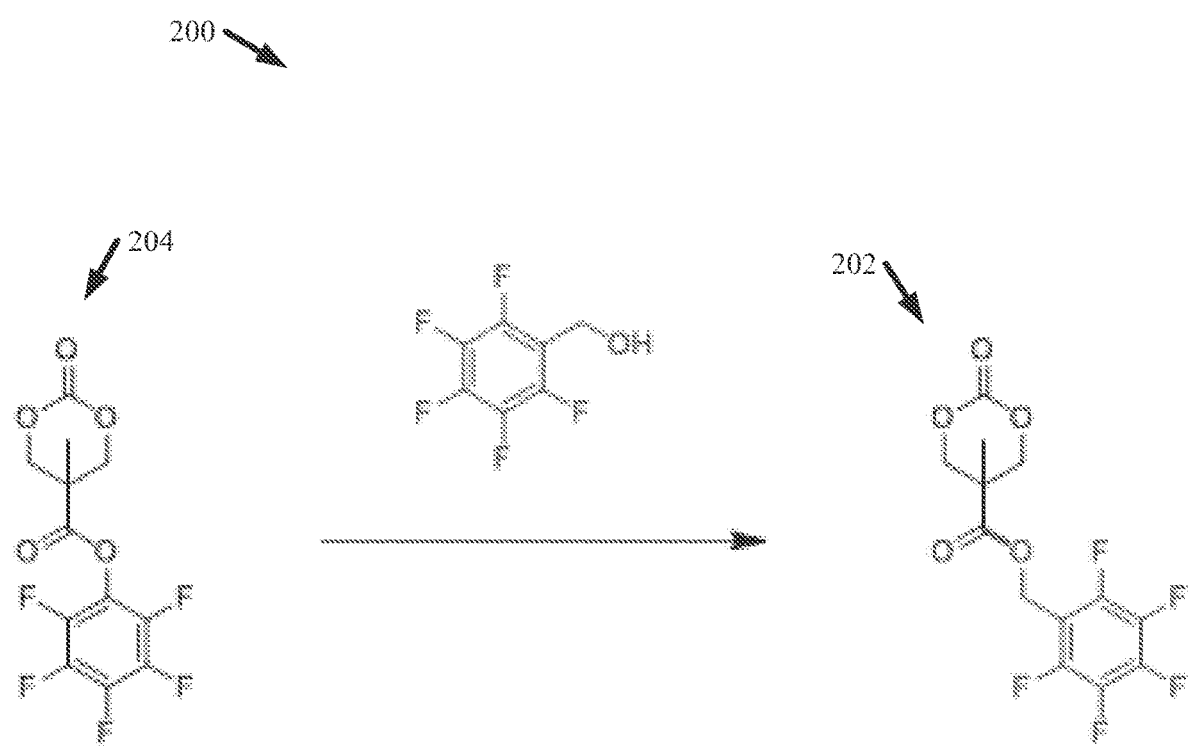
FIG. 2 illustrates a diagram of an example, non-limiting chemical-forming scheme that can facilitate generating one or more monomers in accordance with the one or more embodiments described herein.

FIG. 2 illustrates a diagram of an example, non-limiting compound-forming scheme 200 that can facilitate generating one or more cyclic monomers (e.g., cyclic carbonate monomer 202) that can be characterized by chemical formula 100. Repetitive description of like elements employed in other embodiments described herein is omitted for sake of brevity. While one or more particular monomer reactants (e.g., monomer reactant 204), perfluoroaryl alcohols, solvents, and/or catalysts are depicted; additional embodiments of compound-forming scheme 200 are also envisaged. For example, the principal mechanism of compound-forming scheme 200 can be applied to other monomer reactants (e.g., carbonate monomer), perfluoroaryl alcohols, solvents, and/or catalysts in accordance with the various features described herein.

As shown in FIG. 2, compound-forming scheme 200 can depict reacting one or more monomer reactants (e.g., monomer reactant 204) with one or more perfluoroaryl alcohols to form one or more cyclic monomers that can be characterized by chemical formula 100 (e.g., cyclic carbonate monomer 202). The one or more monomer reactants can be cyclic carbonates. Additionally, the one or more monomer reactants can comprise a perfluoroaryl group directly bonded to a molecular backbone. For example, monomer reactant 204 comprises a perfluorophenyl group directly bonded to its molecular backbone. The one or more perfluoroaryl alcohols can comprise a perfluoroaryl group covalently bonded to one or more hydroxyl groups. For example, the perfluoroaryl alcohol can be pentafluorobenzyl alcohol, as shown in FIG. 2.

The one or more monomer reactants (e.g., one or more monomer reactants 204) and the one or more perfluoroaryl alcohols (e.g., one or more pentafluorobenzyl alcohols) can be dissolved in a solvent in the presence of a catalyst. The solvent can be an organic solvent such as tetrahydrofuran (THF). Additionally, the catalyst can be an organocatylst such as tetra-n-butylammonium fluoride (TBAF). For example, the catalyst can be present in a molar percent ranging from 5 molar percent to 20 molar percent. Additionally, the reaction of compound-forming scheme 200 can be facilitated by stirring the one or more monomer reactants (e.g., one or more monomer reactants 204), the one or more perfluoroaryl alcohols (e.g., one or more pentafluorobenzyl alcohols), the solvent, and/or the catalyst at a temperature greater than or equal to 10 degrees Celsius (° C.) and less than or equal to 150° C. for a period of time ranging from two minutes to 48 hours.

For example, the cyclic carbonate monomer 202 can be formed in accordance with compound-forming scheme 200 under the following exemplary conditions. A 250 milliliter (mL) curved bottom flask can be equipped with a magnetic stir-bar and charged with: 6.5 grams of monomer reactant 204 at 19.9 millimoles (mmol), 4.5 grams of pentafluorobenzyl alcohol at 22.7 mmol, and 30 mL of THF. Further, 2.0 mL of TBAF at 2 mmol and/or 1 moles per liter (M) can be added. The reaction mixture can be stirred at room temperature (RT) for 24 hours. The solvent can then be removed with the aid of a rotary evaporator, and the crude residue can be purified by column chromatography to afford the desired product as a white solid. The cyclic carbonate monomer 202 can further be purified via recrystallization from an ethyl acetate-hexane mixture.

Figure 3:
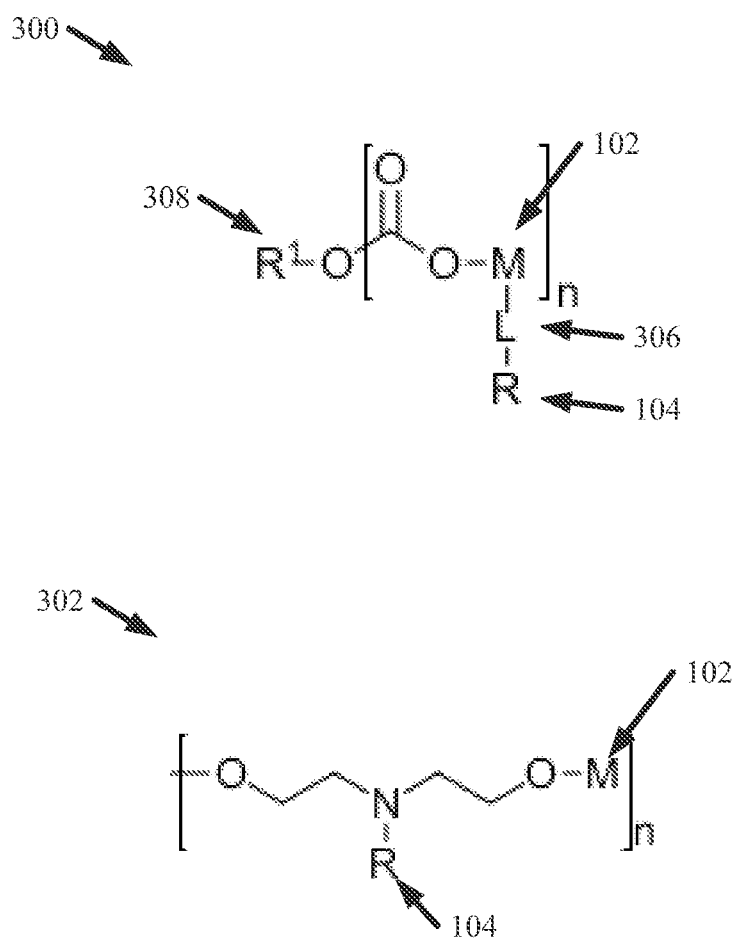
FIG. 3 illustrates a diagram of example, non-limiting chemical structures that can characterize one or more polymers in accordance with one or more embodiments described herein.

FIG. 3 illustrates a diagram of example, non-limiting chemical formulas that can characterize polymers with perfluoroaryl groups in accordance with one or more embodiments described herein. Repetitive description of like elements employed in other embodiments described herein is omitted for sake of brevity. Chemical formula 300 can characterize one or more polycarbonate polymers with one or more perfluoroaryl groups. Chemical formula 302 can characterize one or more polyurethane polymers with one or more perfluoroaryl groups. As shown in FIG. 3, "n" can represent an integer greater than or equal to two and less than or equal to one thousand. The one or more polymers that can be characterized by chemical formula 300 and/or chemical formula 302 be homopolymers and/or copolymers, such as, but not limited to: alternate copolymers, random copolymers, block copolymers (e.g., deblock copolymers and/or triblock copolymers), and/or the like.

Figure 4:
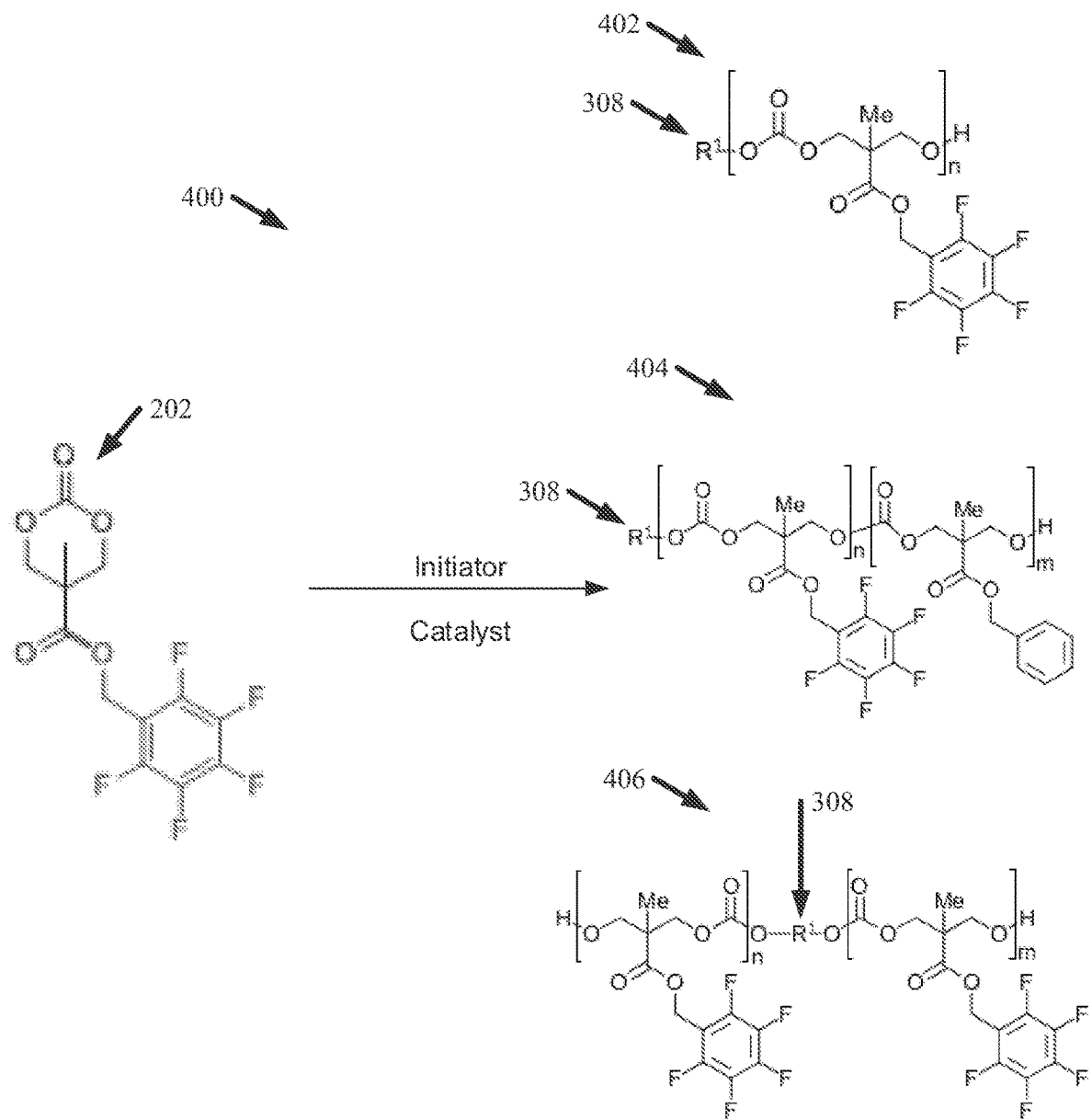
FIG. 4 illustrates a diagram of example, non-limiting polymerization schemes that can facilitate generating one or more polymers in accordance with one or more embodiments described herein.

As shown in FIG. 3, one or more polymers that can be characterized by chemical formula 300 can comprise a plurality of carbonate groups covalently bonded to a molecular backbone 102 (e.g., represented by "M" in FIG. 4). Further, one or more polycarbonates that can be characterized by chemical formula 300 can comprise one or more pendent functional group 104 (e.g., represented by "R"). As described with reference to FIG. 1, the one or more pendent functional groups 104 can comprise a perfluoroaryl group and a methylene group. For example, the one or more pendent functional groups 104 can be perfluorobenzyl groups.

The one or more pendent functional groups 104 can be bonded to the molecular backbone 102 by one or more linkage group 306. The one or more linkage groups 306 can comprise alkyl and/or aryl structures. For example, the one or more linkage groups 306 can comprise, but are not limited to: carboxyl groups, carbonyl groups, ester groups, ether groups, ketone groups, amine groups, phosphine groups, urea groups, carbonate groups, alkenyl groups, hydroxyl groups, a combination thereof, an/or the like.

Furthermore, one or more polycarbonate polymers that can be characterized by chemical formula 300 can comprise one or more functional groups 308 covalently bonded to the molecular backbone 102 (e.g., via one or more carbonate groups). As shown in FIG. 3, "$R^1$" can represent the one or more functional groups 308. The one or more functional groups 308 can comprise alkyl and/or aryl structures. For example, the one or more functional groups 308 can comprise, but are not limited to: carboxyl groups, carbonyl groups, ester groups, ether groups, ketone groups, amine groups, phosphine groups, urea groups, carbonate groups, alkenyl groups, hydroxyl groups, a combination thereof, an/or the like. For example, the functional groups 308 can be derived from $mPEG_{5K}$, $mPEG_{10K}$, and/or benzyl alcohol.

As shown in FIG. 3, one or more polymers that can be characterized by chemical formula 302 can comprise a plurality of urethane groups. The plurality of urethane groups can be covalently bonded to a molecular backbone 102 (e.g., represented by "M" in FIG. 3). Further, the one or more polyurethane polymers that can be characterized by chemical formula 302 can comprise one or more pendent functional groups 104 (e.g., represented by "R" in FIG. 3). As described with reference to FIG. 1, the one or more pendent functional groups 104 can comprise a perfluoroaryl group and a methylene group. For example, the one or more pendent functional groups 104 can be perfluorobenzyl groups. The one or more pendent functional groups 104 can be bonded to one or more amine groups of the one or more urethane structures (e.g., as shown in FIG. 3).

FIG. 4 illustrates a diagram of an example, non-limiting polymerization scheme 400 that can facilitate generating one or more polycarbonate polymers (e.g., first polycarbonate 402, second polycarbonate 404, and/or third polycarbonate 406) that can be characterized by chemical formula 300 in accordance with one or more embodiments described herein. Repetitive description of like elements employed in other embodiments described herein is omitted for sake of brevity. As shown in FIG. 4, "n" can represent an integer greater than or equal to two and less than or equal to one thousand; and "Me" can represent a methyl group. While one or more particular reactants (e.g., cyclic carbonate monomer 202) are depicted; additional embodiments of polymerization scheme 400 are also envisaged. For example, the principal mechanism of polymerization scheme 400 can be applied to other reactants (e.g., monomers that can be characterized by chemical formula 100) in accordance with the various features described herein.

Polymerization scheme 400 can facilitate generating homopolymers (e.g., first polycarbonate 402) and/or copolymers (e.g., diblock polymers such as second polycarbonate 404 and/or triblock polymers such as third polycarbonate 406). Polymerization scheme 400 comprises polymerizing a cyclic monomer that can be characterized by chemical formula 100 (e.g., cyclic carbonate monomer 202) with an initiator, in the presence of a catalyst, to form a polycarbonate that can be characterized by chemical formula 300 (e.g., first polycarbonate 402, second polycarbonate 404, and/or third polycarbonate 406). For example, the polymerization scheme 400 can comprise a ring-opening polymerization (ROP) of one or more cyclic monomers that can be characterized by chemical formula 100 (e.g., cyclic carbonate monomer 202) with one or more initiators to form a polymer and/or copolymer, wherein the functional group 308 (e.g., represented by "$R^1$" in FIG. 4) can be derived from the one or more initiators. Additionally, polymerization scheme 400 can facilitate copolymerizing the one or more cyclic monomers that can be characterized by chemical formula 100 (e.g., cyclic carbonate monomer 202) with additional cyclic monomers, such as cyclic carbonate monomers that are not characterized by chemical formula 100 (e.g., benzyl carbonate monomers), to form one or more copolymers (e.g., the diblock copolymer, second polycarbonate 404).

The one or more initiators can be microinitiators. Further, the one or more initiators can be block polymers and comprise a water-soluble block. For example, the one or more initiators can comprise poly(ethylene glycol) (PEG) with various molecular weights. For example, the one or more initiators can comprise PEG with a molecular weight ranging from 4,800 grams per mole (g/mol) to 5,500 g/mol ($mPEG_{5K}$). In another example, the one or more initiators can comprise PEG with a molecular weight ranging from 9,500 g/mol to 10,500 g/mol ($mPEG_{10K}$). Moreover, the one or more initiators can comprise a functional group, such as a hydroxy group, to facilitate the polymerization. Additionally, the catalyst can be an organocatylst such as, but not limited to: 1,8-diazabicyclo[5.4.0]undec-7-ene (DBU); trifluoromethanesulfonic acid (TfOH); a potassium salt of TU (TU-A). For example, the catalyst can be present in a molar percent ranging from 5 molar percent to 20 molar percent.

To facilitate the polymerization (e.g., the ROP) the polymerization scheme 400 can comprise dissolving the one or more cyclic monomers (e.g., cyclic carbonate monomer 202), the one or more initiators, and/or the catalyst in a solvent. The solvent can be an organic solvent such as 1-(3,5-bis(trifluoromethyl)-phenyl)-3-cyclohexyl-2-thiourea (TU). Further, the polymerization of polymerization scheme 400 can be facilitated by stirring the one or more cyclic monomers (e.g., cyclic carbonate monomer 202), the one or more initiators, the catalyst, and/or the solvent at a temperature greater than or equal to 10 degrees Celsius (° C.) and less than or equal to 150° C. for a period of time ranging from two minutes to 48 hours.

For example, the first polycarbonate 402 can be formed in accordance with polymerization scheme 400 under the following exemplary conditions. In a nitrogen-filled glovebox, a 20 mL scintillation vial equipped with a magnetic stir-bar can be charged with: 500 mg of hydroxyl $mPEG_{5K}$ at 0.10 mmol; 340 mg of cyclic carbonate monomer 202 at 1.0 mmol; 18.7 mg of TU at 0.05 mmol; and 1.0 mL of $CH_2Cl_2$. The reaction mixture can be stirred at RT until all the solids had dissolved. Additionally, 7.5 micro liters μL of DBU at 0.05 mmol can be added to initiate the polymerization. After stirring at RT for 15 min, the vial can be removed from the glovebox and quenched with excess benzoic acid. The polymer can be precipitated twice from 40 mL of diethylether to afford the desired material as a white solid. Moreover, the polymer can be further purified by dialysis against 1:1 acetonitrile:isopropyl alcohol.

FIG. 5 illustrates a diagram of an example, non-limiting chart 500 that can depict polymerization conditions for various polymerizations in accordance with polymerization scheme 400 and/or structural characteristics for various polycarbonates (e.g., that can be characterized by chemical formula 300) that can be formed as a result of said polymerization conditions. Repetitive description of like elements employed in other embodiments described herein is omitted for sake of brevity.

The first column 502 of chart 500 can depict the polycarbonate sample subject to evaluation. The second column 504 of chart 500 can depict the initiator utilized in the subject polymerization. The third column 506 of chart 500 can depict the catalyst utilized in the subject polymerization. The fourth column 508 of chart 500 can depict a ratio ([I]:[M]) of initiator ([I]) to cyclic monomer ([M]). Regarding the sixth and/or seventh polycarbonate samples, the fourth column 508 can depict a ration ([I]:[$M_1$]:[$M_2$]) of initiator ([I]) to a first cyclic monomer ([$M_1$]) (e.g., cyclic carbonate monomer 202) and to a second cyclic monomer ([$M_2$]) (e.g., 5-methyl-5-benzyloxycarbonyl-1,3-dioxan-2-one). The fifth column 510 of chart 500 can depict the duration of the subject polymerization. The sixth column 512 of chart 500 can depict the percent of cyclic monomers converted to polycarbonates. The conversion percentage of the sixth column 512 can be determined by proton nuclear magnetic resonance ($H^1$ NMR). The seventh column 514 of chart 500 can depict a degree of polymerization (Dp) for the subject polymerization. The eighth column 516 of chart 500 can depict a number average molecular weight ($M_n$) in g/mol of the subject polycarbonate sample as analyzed by nuclear magnetic resonance (NMR). The ninth column 518 of chart 500 can depict $M_n$ in g/mol of the subject polycarbonate sample as analyzed by gel permeation chromatography (GPC). The tenth column 520 of chart 500 can depict molecular weight distribution/dispersity (D) of the subject polycarbonate sample. As evident from chart 500, an analysis of $M_n$ versus conversion percentage of the cyclic monomer (e.g., cyclic carbonate monomer 202) can indicate a high level of control over the polymerization and resulting molecular weights facilitated by polymerization scheme 400.

Figure 6:
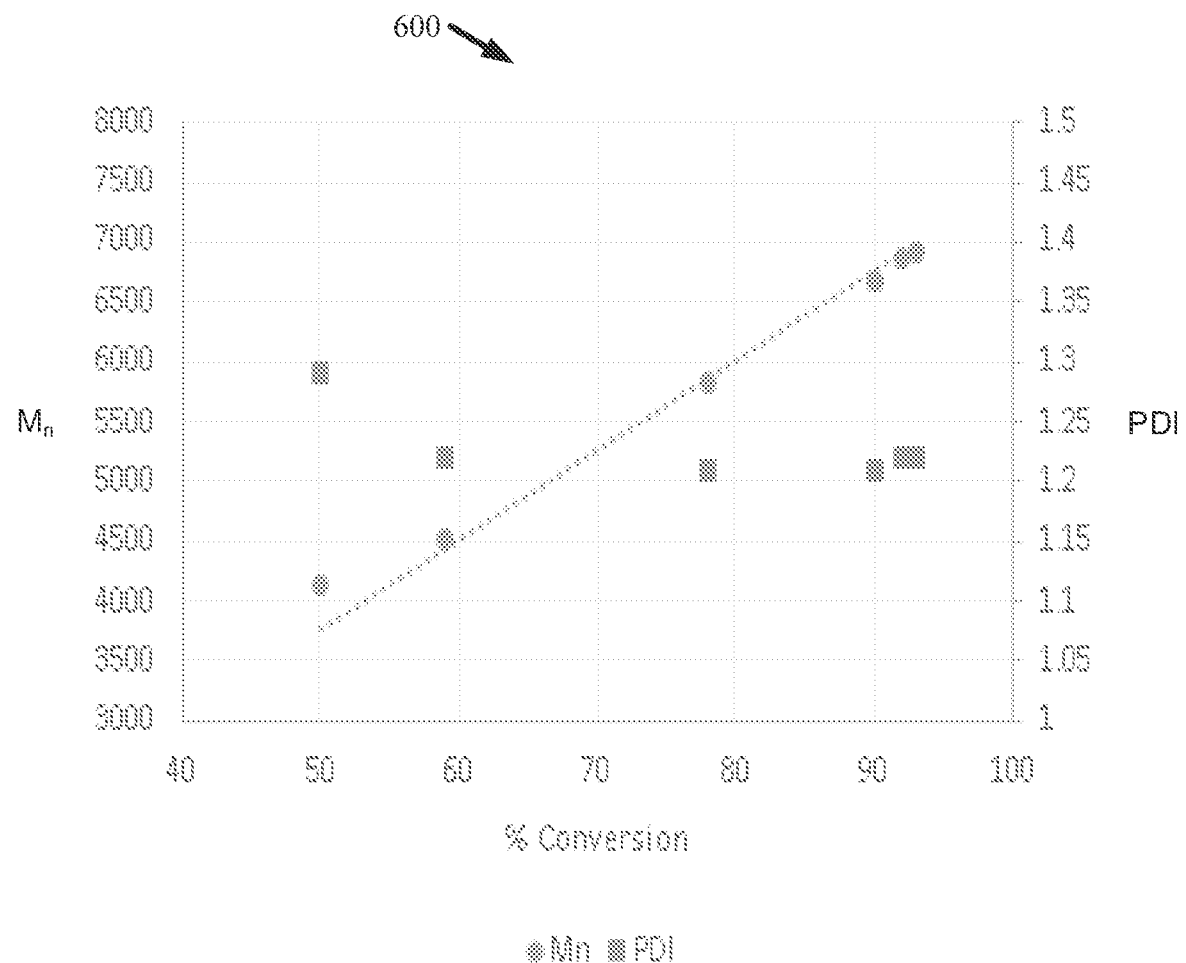
FIG. 6 illustrates a diagram of an example, non-limiting graph that can depict structural characteristics of one or more polymers in accordance with the one or more embodiments described herein.

FIG. 6 illustrates a diagram of an example, non-limiting graph 600 that can depict various structural characteristics of polycarbonate samples illustrated in chart 500. Repetitive description of like elements employed in other embodiments described herein is omitted for sake of brevity. Graph 600 can plot conversion of the cyclic monomer (e.g., cyclic carbonate monomer 202) versus $M_n$ and a polydispersity index (PDI). Graph 600 can regard a polymerization performed in accordance with polymerization scheme 400, wherein benzyl alcohol can be used as the initiator, TU can be used as the solvent, and 5 mol % of DBU can be used as the catalyst.

Figure 7:
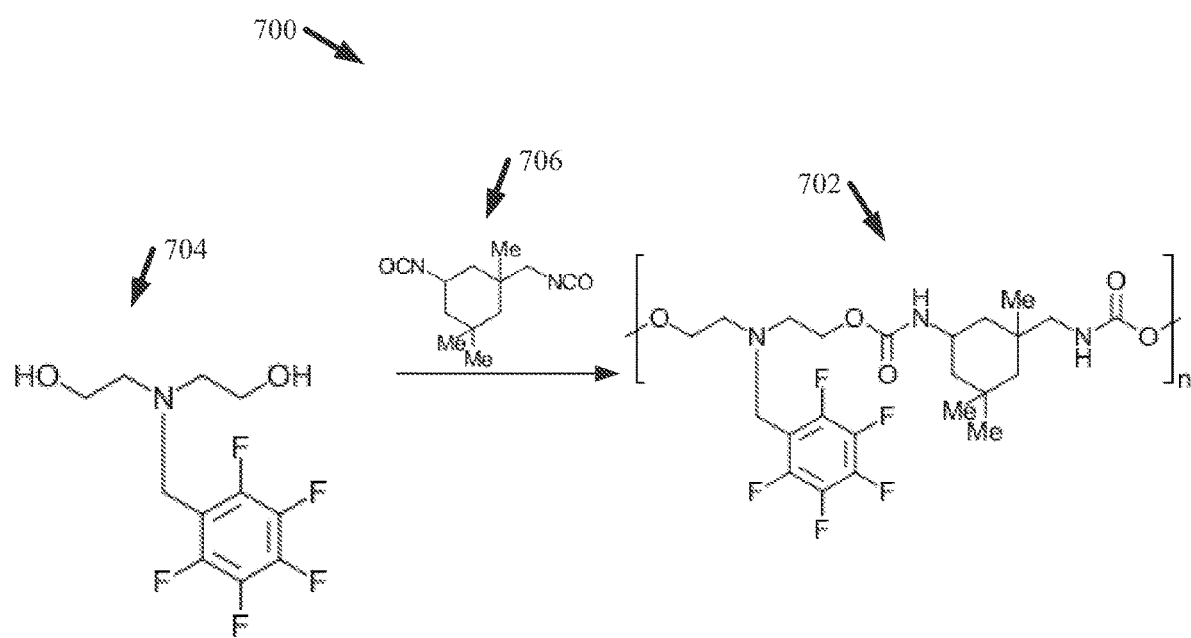
FIG. 7 illustrates a diagram of an example, non-limiting polymerization scheme that can facilitate generating one or more polymers in accordance with one or more embodiments described herein.

FIG. 7 illustrates a diagram of an example, non-limiting polymerization scheme 700 that can facilitate generating one or more polyurethane polymers (e.g., first polyurethane 702) that can be characterized by chemical formula 302. Repetitive description of like elements employed in other embodiments described herein is omitted for sake of brevity. While one or more particular reactants (e.g., urethane reactant 704) and/or isocyanates are depicted; additional embodiments of polymerization scheme 700 are also envisaged. For example, the principal mechanism of polymerization scheme 700 can be applied to other reactants (e.g., urethane monomers comprising a pendent functional group 104) and/or isocyanates in accordance with the various features described herein. As shown in FIG. 7, "n" can represent an integer greater than or equal to two and less than or equal to one thousand.

Polymerization scheme 700 can comprise polymerizing one or more urethane monomers comprising a pendent functional group 104 (e.g., urethane reactant 704) with one or more isocyanates (e.g., first isocyanate 706) to form one or more polyurethane polymer that can be characterized by chemical formula 302 (e.g., first polyurethane 702). The one or more polyurethane polymers generated by polymerization scheme 700 can be copolymers (e.g., alternating copolymers, random copolymers, and/or block copolymers). The one or more isocyanates (e.g., first isocyanate 706) can comprise alkyl and/or aryl structures. Further, the one or more isocyanates can be diisocyanates. Polymerization of the one or more urethane monomers (e.g., urethane reactant 704) with the one or more isocyanates (e.g., first isocyanate 706) can form a polyurethane polymer (e.g., first polyurethane 702) comprising one or more carbamate groups (e.g., as shown in FIG. 7).

The polymerization of polymerization scheme 700 can be facilitated by dissolving the one or more urethane monomers (e.g., urethane reactant 704), the one or more isocyanates (e.g., first isocyanate 706), and/or a catalyst in a solvent to form a mixture. The catalyst can be an organocatalyst such as DBU (e.g., a catalyst system comprising a mole percent of DBU greater than or equal to one percent and less than or equal to twenty-five percent). The solvent can be an organic solvent such as TU, dichloromethane, a combination thereof, and/or the like. Additionally, the mixture can be stirred at a temperate greater than or equal to 10° C. and less than or equal to 150° C. (e.g., room temperature (RT)) for a period of time greater than or equal to 5 minutes and less than or equal to 48 hours (e.g., 18 hours). For example, the polymerization scheme 700 can facilitate generating the first polyurethane 702 having a number average molecular weight ($M_n$) of 60,413 g/mol, a weight average molecular weight ($M_w$) of 92,430 g/mol, and a polydispersity index (PDI) of 1.52.

In one or more embodiments, the urethane reactant 704 that can be utilized in accordance with polymerization scheme 700 can be prepared under the following exemplary conditions, and/or like conditions. A 250 mL curved bottom flask equipped with a magnetic stir-bar can be charged with: 1.45 mL of diethanolamine at 15 mmol; 2.9 grams of potassium carbonate at 21 mmol; and 40 mL of acetonitrile. Further, 2.26 mL of pentafluorobenzyl bromide at 15 mmol can be added, and the reaction mixture can be stirred for 36 hours at RT. The reaction mixture can be filtered and concentrated with the aid of a rotary evaporator. The crude residue can be filtered through a silica gel plug eluting with 10% acetone in hexane.

The first polyurethane 702 can be formed in accordance with polymerization scheme 700 under the following exemplary conditions and/or like conditions. In a nitrogen-filled glovebox a 20 mL scintillation vial can be charged with: 285 milligrams (mg) of one or more urethane monomers comprising one or more pendent functional groups 104 (e.g., urethane reactant 704) at 1.0 mmol; 209 microliters (μL) of isopherone diisocyanate at 1.0 mmol; and 1 mL of dichloromethane. Also, 3 μL of DBU at 0.02 mmol can be added, and the reaction mixture can be stirred for 18 hours at RT. The reaction mixture can then be removed from the glovebox and the polymer can be precipitated twice from hexanes to afford and off-white solid. This material can be further purified via dialysis 1:1 acetonitrile:isopropyl alcohol to afford a light yellow film.

Figure 8:
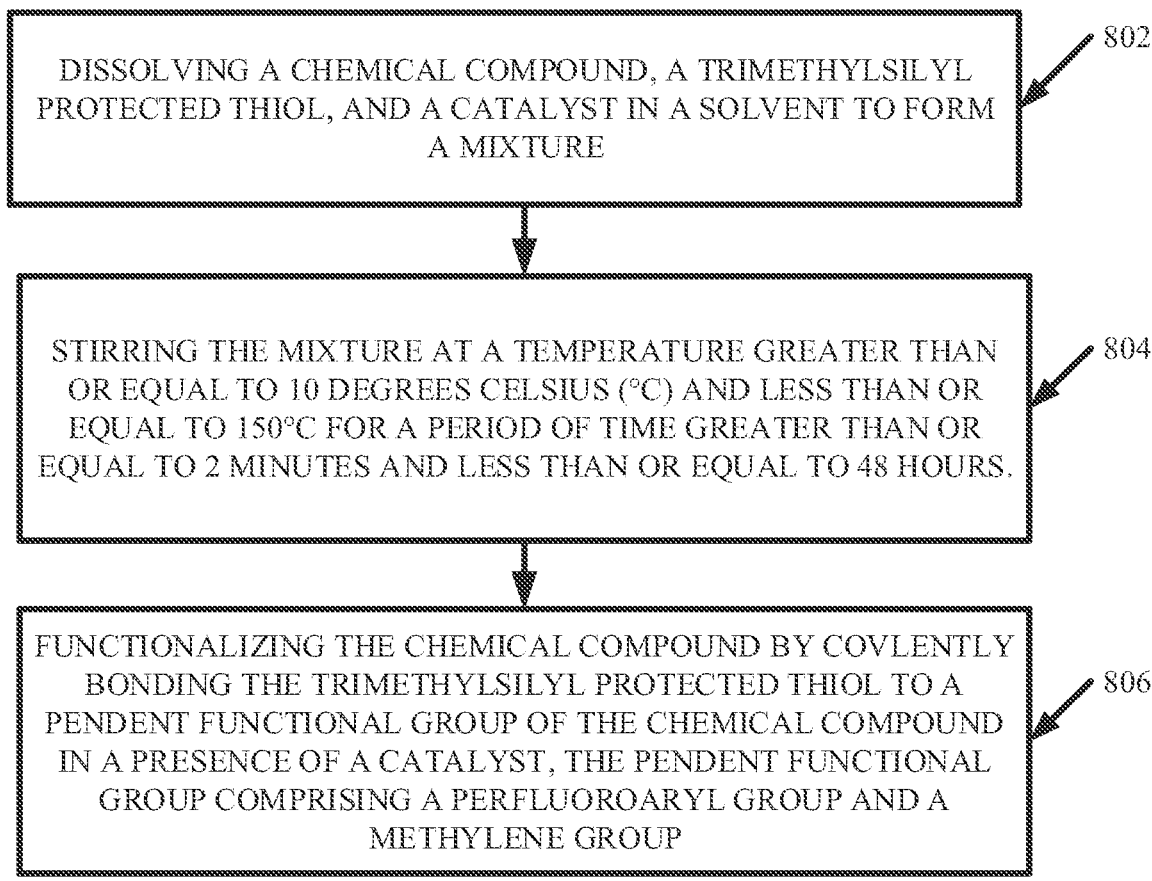
FIG. 8 illustrates a flow diagram of an example, non-limiting method that can facilitate post-synthesis functionalization of one or more chemical compounds in accordance with one or more embodiments described herein.

FIG. 8 illustrates a flow diagram of an example, non-limiting method 800 that can facilitate post-synthesis functionalization of one or more chemical compounds in accordance with one or more embodiments described herein. Repetitive description of like elements employed in other embodiments described herein is omitted for sake of brevity. For example, method 800 can be utilized to functionalize monomers that can comprise one or more pendent functional groups 104. In another example, method 800 can be utilized to functionalize polycarbonates that can be characterized by chemical formula 300. In another example, method 800 can be utilized to functionalize polyurethanes that can be characterized by chemical formula 302.

At 802, the method 800 can comprise dissolving a chemical compound (e.g., characterized by chemical formula 300 and/or 302) and one or more trimethylsilyl protected thiols in a solvent to form a mixture. The chemical compound can comprise one or more monomers and/or one or more polymers (e.g., characterized be chemical formula 300 and/or 302), which can comprise one or more pendent functional groups 104 (e.g., perfluorobenzyl groups). For example, the chemical compound can comprise first polycarbonate 402, second polycarbonate 404, third polycarbonate 406, first polyurethane 702, a combination thereof, and/or the like. The one or more pendent functional groups 104 comprising the chemical compound can serve as a handle to facilitate functionalization via method 800.

The one or more trimethylsilyl protected thiols can comprise a functional group, which can comprise: alkyl structures, aryl structures, carboxyl groups, carbonyl groups, amine groups, amide groups, ether groups, ester groups, ketone groups, hydroxyl groups, alkenyl groups, aldehyde groups, alkene groups, a combination thereof, and/or the like. For example, the one or more trimethylsilyl protected thiols can be trimethylsilyl protected dodecanethiol. The solvent can be an organic solvent. Example solvents can include, but are not limited to: dimethylformamide (DMF), N-methyl-2-pyrrolidone (NMP), a combination thereof, and/or the like.

In one or more embodiments, the mixture at 802 can be catalyst-free. However, wherein the mixture is catalyst-free, the functionalization achieved by method 800 can depend on the synthesis method of the chemical compound. For example, wherein the chemical compound is prepared via an acid-catalyzed ROP (e.g., first polycarbonate sample in shown in chart 500), method 800 can achieve little conversion of the chemical compound's pendent functional groups 104. In another example, wherein the chemical compound is prepared via base-catalyzed polymerization conditions (e.g., second polycarbonate sample shown in chart 500), method 800 can achieve high reactivity between the chemical compound and the one or more trimethylsilyl protected thiols, thereby rendering high conversion percentages. In various embodiments, a catalyst can be added to the mixture 802 to facilitate functionalization via method 800. The catalyst can be a basic salt, such as but, not limited to, DBU-based salts and/or potassium benzoate salts.

At 804, the method 800 can comprise stirring the mixture at a temperature greater than or equal to 10° C. and less than or equal to 150° C. for a period of time greater than or equal to 2 minutes and less than or equal to 48 hours. For example, at 804 the method 800 can comprise stirring the mixture at RT for five minutes.

At 806, the method 800 can comprise functionalizing the chemical compound by covalently bonding the one or more trimethylsilyl protected thiols to one or more pendent functional groups 104 of the chemical compound in the presence of a catalyst. For example, the chemical compound can be characterized by chemical formula 300. In another example, the chemical compound (e.g., comprising a polymer or monomer) can be characterized by chemical formula 302. In another example, the chemical compound can comprise a molecular backbone bonded to one or more pendent functional groups 104, wherein the molecular backbone can comprise: one or more carbonate structures, one or more urethane structures, one or more amide structures, one or more ester structures, one or more ether structures, one or more acrylate structures, and/or one or more styrene structures. The catalyst can originate from an addition to the mixture at 802 and/or from a synthesis reaction that generated the chemical compound. The functionalization at 806 can generate mono-substituted products and/or poly-substituted products. As used herein "mono-substituted" can refer to the substitution of a single fluoride of a subject pendent functional group 104. For example, mono-substituted products generated at 806 can comprise a pendent functional group 104 covalently bonded to a single trimethylsilyl protected thiol. As used herein "poly-substituted" can refer to the substitution of multiple fluorides of a subject pendent functional group 104. For example, poly-substituted products generated at 806 can comprise a pendent functional group 104 covalently bonded to a plurality of trimethylsilyl protected thiols. Also, as used herein "bi-substituted" can refer to the substitution of two fluorides of a subject pendent functional group 104. Further, as used herein "tri-substituted" can refer to the substitution of three fluorides of a subject pendent functional group 104.

As shown in Table 1, presented below, the amount of catalyst in the mixture at 802 (e.g., originating from an addition of catalyst and/or residual catalyst from a synthesis reaction) can affect the functionalization at 806. For example, Table 2 can regard a chemical compound prepared via an acid-catalyzed ROP (e.g., first polycarbonate sample in shown in chart 500), wherein DBU and/or a benzoate catalyst is added to the mixture at 802 in various mole percentages (mol %). As described above, without the addition of DBU and/or benzoate catalysts, the chemical compound evaluated by Table 1 would exhibit little to no functionalization at 806. However, with even a small amount of DBU and/or a benzoate catalyst (e.g., 0.5 mol %), the chemical compound can be effectively functionalized at 806.

Additionally, the amount of catalyst in the mixture at 802 (e.g., originating from an addition of catalyst and/or residual catalyst from a synthesis reaction) can affect the number of mono-substituted products and/or poly-substituted products generated by the functionalization at 806. In Table 1, "I" can represent mono-substituted products and/or "II" can represent poly-substituted products.

The ratio of mono-substituted products to poly-substituted products, as shown in Table 1, can be determined by fluorine nuclear magnetic resonance (F NMR). Additionally, $DBU \cdot PhCO_2H$ can represent a salt of DBU and benzoic acid. As shown in Table 1, an increased presence of catalyst can directly increase the number of substitutions (e.g., the number of poly-substituted products) achieved by the functionalization at 806.

Figure 9:
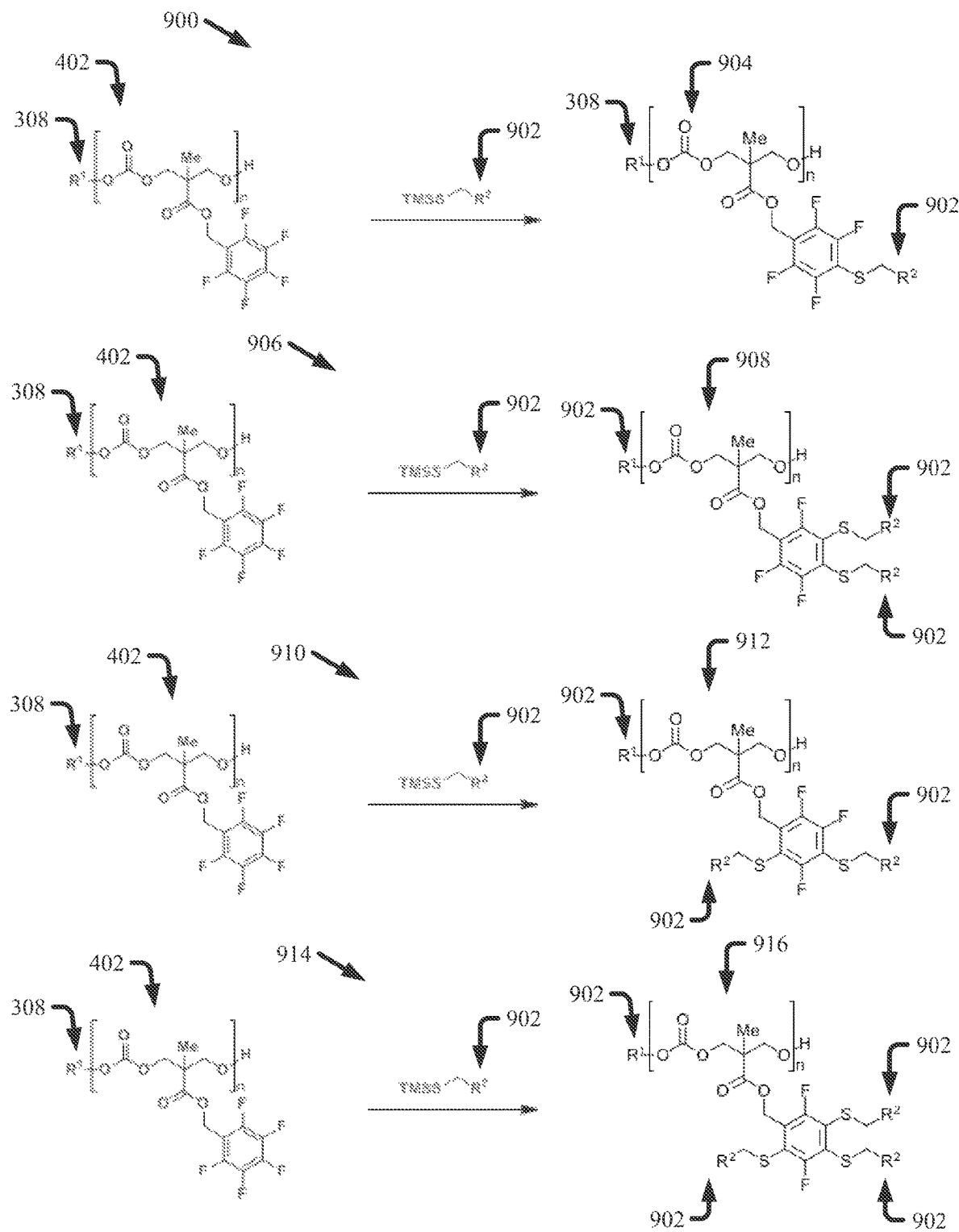
FIG. 9 illustrates a diagram of example, non-limiting functionalization schemes that can facilitate post-synthesis functionalization of one or more chemical compounds in accordance with one or more embodiments described herein.

FIG. 9 illustrates a diagram of example, non-limiting functionalization schemes that can facilitate functionalization of one or more polycarbonates (e.g., that can be characterized by chemical formula 300) in accordance with one or more embodiments described herein (e.g., method 800). Repetitive description of like elements employed in other embodiments described herein is omitted for sake of brevity. While one or more particular reactants (e.g., first polycarbonate 402) are depicted; additional embodiments of the functionalization schemes shown in FIG. 9 are also envisaged. For example, the principal mechanisms of the functionalization schemes shown in FIG. 9 can be applied to other reactants (e.g., other polycarbonates that can be characterized by chemical formula 300) in accordance with the various features described herein. As shown in FIG. 9, "n" can represent an integer greater than or equal to two and less than or equal to one thousand.

In each of the functionalization schemes of FIG. 9, one or more polycarbonates that can be characterized by chemical formula 300, one or more trimethylsilyl protected thiols, and/or a catalyst can be dissolved in a solvent to form a mixture. The catalyst can be an organocatalyst and comprise a basic salt, such as a DBU-based salt. The solvent can be organic and/or polar. Example solvents include, but are not limited to DMF, NMP, a combination thereof, and/or the like. To facilitate functionalization, the mixture can be stirred at a temperate greater than or equal to 10° C. and less than or equal to 150° C. (e.g., RT) for a period of time greater than or equal to 2 minutes and less than or equal to 48 hours (e.g., 5 minutes).

The first functionalization scheme 900 can depict a functionalization of a polycarbonate that can be characterized by chemical formula 300 (e.g., first polycarbonate 402) with one or more trimethylsilyl protected thiols (represented by "TMSS" in FIG. 9), which can comprise one or more second functional group 902 (e.g., represented by "$R^2$" in FIG. 9), to form a mono-substituted product (e.g., fourth polycarbonate 904). The second functional group 902 can comprise: alkyl structures, aryl structures, carboxyl groups, carbonyl groups, amine groups, amide groups, ether groups, ester groups, ketone groups, hydroxyl groups, alkenyl groups, aldehyde groups, alkene groups, a combination thereof, and/or the like. For example, the one or more second functional groups 902 can be undecane, thereby the one or more trimethylsilyl protected thiols can be trimethylsilyl protected dodecanethiol.

The second functionalization scheme 906 can depict a functionalization of a polycarbonate that can be characterized by chemical formula 300 (e.g., first polycarbonate 402) with one or more trimethylsilyl protected thiols (represented by "TMSS" in FIG. 9), which can comprise one or more second functional group 902 (e.g., represented by "$R^2$" in FIG. 9), to form a bi-substituted product (e.g., fifth polycarbonate 908). The second functional group 902 can comprise: alkyl structures, aryl structures, carboxyl groups, carbonyl groups, amine groups, amide groups, ether groups, ester groups, ketone groups, hydroxyl groups, alkenyl groups, aldehyde groups, alkene groups, a combination thereof, and/or the like. For example, the one or more second

TABLE 1

| Entry | Catalyst | Mol % | Ratio I:II |
|---|---|---|---|
| 1 | DBU | 54 | 0.55 |
| 2 | DBU•PhCO$_2$H | 100 | 0.82 |
| 3 | DBU•PhCO$_2$H | 18 | 1.1 |
| 4 | DBU•PhCO$_2$H | 10 | 2 |
| 5 | DBU•PhCO$_2$H | 5 | 2.5 |
| 6 | DBU•PhCO$_2$H | 2.5 | 10 |
| 7 | DBU•PhCO$_2$H | 1 | I only |
| 8 | DBU•PhCO$_2$H | 0.5 | I only | functional groups 902 can be undecane, thereby the one or more trimethylsilyl protected thiols can be trimethylsilyl protected dodecanethiol.

The third functionalization scheme 910 can depict a functionalization of a polycarbonate that can be characterized by chemical formula 300 (e.g., first polycarbonate 402) with one or more trimethylsilyl protected thiols (represented by "TMSS" in FIG. 9), which can comprise one or more second functional group 902 (e.g., represented by "$R^2$" in FIG. 9), to form another bi-substituted product (e.g., sixth polycarbonate 912). The second functional group 902 can comprise: alkyl structures, aryl structures, carboxyl groups, carbonyl groups, amine groups, amide groups, ether groups, ester groups, ketone groups, hydroxyl groups, alkenyl groups, aldehyde groups, alkene groups, a combination thereof, and/or the like. For example, the one or more second functional groups 902 can be undecane, thereby the one or more trimethylsilyl protected thiols can be trimethylsilyl protected dodecanethiol.

The fourth functionalization scheme 914 can depict a functionalization of a polycarbonate that can be characterized by chemical formula 300 (e.g., first polycarbonate 402) with one or more trimethylsilyl protected thiols (represented by "TMSS" in FIG. 9), which can comprise one or more second functional group 902 (e.g., represented by "$R^2$" in FIG. 9), to form a tri-substituted product (e.g., seventh polycarbonate 916). The second functional group 902 can comprise: alkyl structures, aryl structures, carboxyl groups, carbonyl groups, amine groups, amide groups, ether groups, ester groups, ketone groups, hydroxyl groups, alkenyl groups, aldehyde groups, alkene groups, a combination thereof, and/or the like. For example, the one or more second functional groups 902 can be undecane, thereby the one or more trimethylsilyl protected thiols can be trimethylsilyl protected dodecanethiol.

For example, a functionalized polycarbonate can be functionalized in accordance with the functionalization schemes shown in FIG. 9 and/or method 800 under the following exemplary conditions and/or like conditions. In a nitrogen filled glovebox, an 8 mL vial equipped with a magnetic stir-bar can be charged with: 25 mg of first polycarbonate 402 at 0.024 mmol; 0.25 mL of NMP; and/or 5 µL of DBU.PhCO$_2$H at 13.2 mg/mL stock solution in NMP and 1 mol % per perfluoroaryl unit catalyst loading. The reaction mixture can be stirred until the solids are dissolved. 17 mg of trimethylsilyl protected dodecanethiol at 0.062 mmol can be added, and the reaction mixture can be stirred at RT for 5 min. The vial can be removed from the glovebox and an aliquot of the reaction mixture was analyzed by F NMR to determine the conversion. The sample was recovered and the crude material was purified via dialysis (1:1 acetonitrile: isopropyl alcohol).

Figure 10:
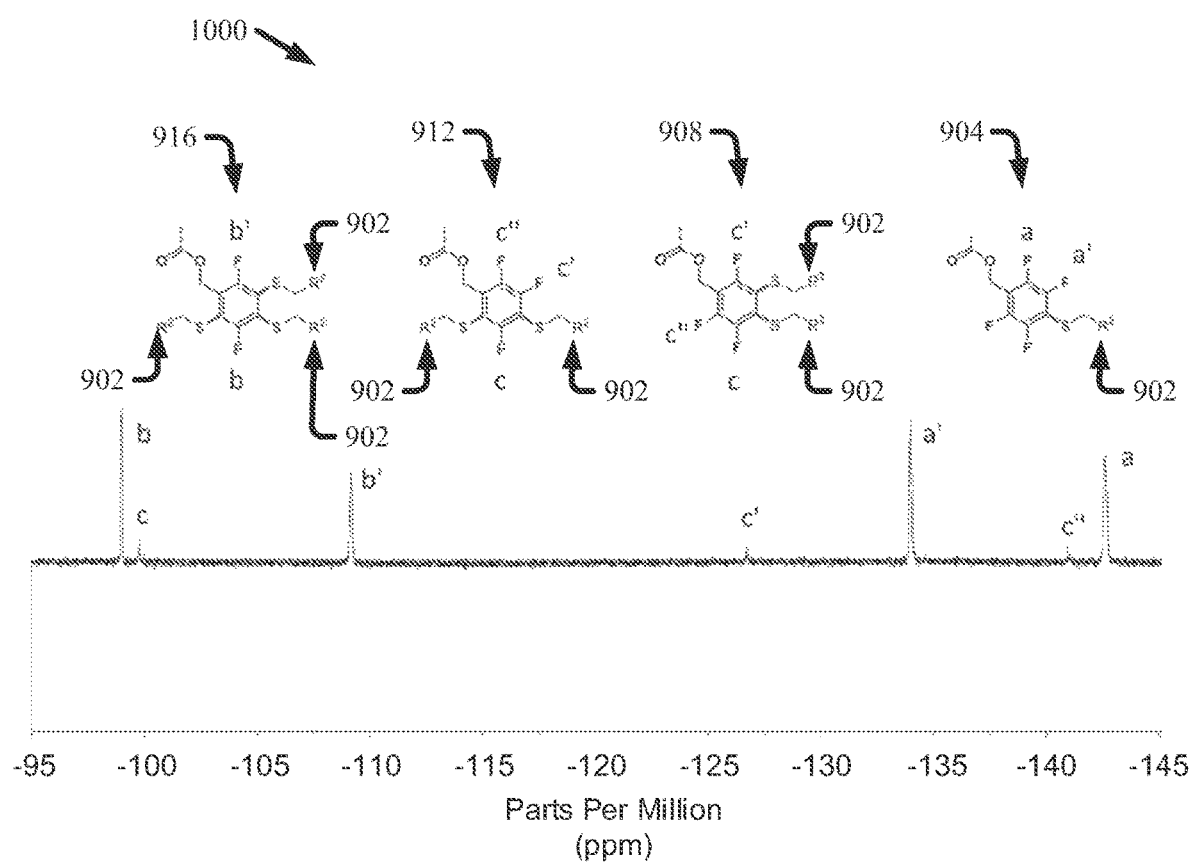
FIG. 10 illustrates a diagram of an example, non-limiting graph that can depict structural characteristics of one or more polymers in accordance with the one or more embodiments described herein.

FIG. 10 illustrates a diagram of an example, non-limiting graph 1000 that can depict structural characteristics of various polycarbonates functionalized in accordance with one or more embodiments described herein (e.g., method 800 and/or one or more of the functionalization schemes shown in FIG. 9). Repetitive description of like elements employed in other embodiments described herein is omitted for sake of brevity. Graph 1000 can show a F NMR spectra for the first polycarbonate 402.

Figure 11:
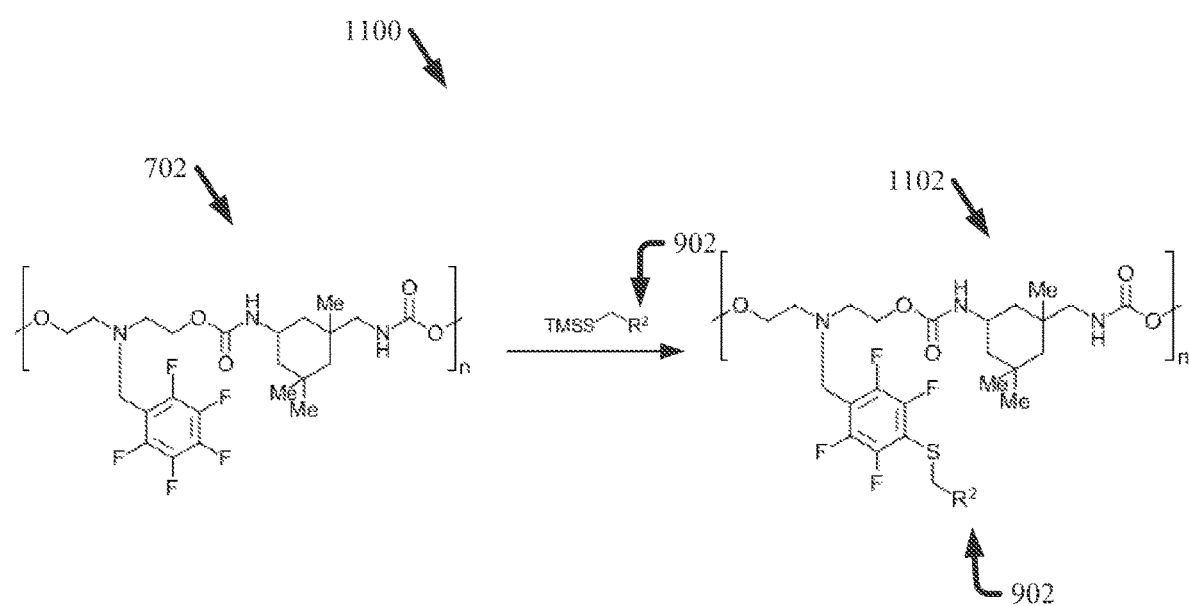
FIG. 11 illustrates a diagram of an example, non-limiting functionalization scheme that can facilitate post-synthesis functionalization of one or more chemical compounds in accordance with one or more embodiments described herein.

FIG. 11 illustrates a diagram of an example, non-limiting functionalization scheme 1100 that can facilitate functionalizing one or more polyurethanes (e.g., that can be characterized by chemical formula 302) in accordance with one or more embodiments described herein (e.g., method 800). Repetitive description of like elements employed in other embodiments described herein is omitted for sake of brevity. While one or more particular reactants (e.g., first polyurethane 702) are depicted; additional embodiments of functionalization scheme 1100 are also envisaged. For example, the principal mechanisms of functionalization scheme 1100 can be applied to other reactants (e.g., other polyurethanes that can be characterized by chemical formula 302) in accordance with the various features described herein. As shown in FIG. 11, "n" can represent an integer greater than or equal to two and less than or equal to one thousand.

Functionalization scheme 1100 can depict a functionalization of one or more polyurethane that can be characterized by chemical formula 302 (e.g., first polyurethane 702) with one or more trimethylsilyl protected thiols (represented by "TMSS" in FIG. 11), which can comprise one or more second functional group 902 (e.g., represented by "$R^2$" in FIG. 11), to form a functionalized polyurethane polymer (e.g., second polyurethane 1102). Similar to the functionalization of one or more polycarbonates, which have a structure that can be characterized by chemical formula 300, can generate mono-substituted products (e.g., fourth polycarbonate 904) and/or poly-substituted products (e.g., fifth polycarbonate 908, sixth polycarbonate 912, and/or seventh polycarbonate 916); the functionalization scheme 1100 can generate mono-substituted polyurethanes (e.g., second polyurethane 1102) and/or poly-substituted polyurethanes (not shown).

The one or more second functional groups 902 can comprise: alkyl structures, aryl structures, carboxyl groups, carbonyl groups, amine groups, amide groups, ether groups, ester groups, ketone groups, hydroxyl groups, alkenyl groups, aldehyde groups, alkene groups, a combination thereof, and/or the like. For example, the one or more second functional groups 902 can be undecane, thereby the one or more trimethylsilyl protected thiols can be trimethylsilyl protected dodecanethiol.

To facilitate functionalization, the one or more polyurethanes that can be characterized by chemical formula 302, the one or more trimethylsilyl protected thiols, and/or a catalyst can be dissolved in a solvent to form a mixture. The catalyst can be an organocatalyst and comprise a basic salt, such as a DBU-based salt and/or sodium dodecanoate. The solvent can be organic and/or polar. Example solvents include, but are not limited to DMF, NMP, a combination thereof, and/or the like. To facilitate functionalization, the mixture can be stirred at a temperate greater than or equal to 10° C. and less than or equal to 150° C. (e.g., RT) for a period of time greater than or equal to 2 minutes and less than or equal to 48 hours (e.g., 5 minutes).

For example, second polyurethane 1102 can be generated in accordance with functionalization scheme 1100 and method 800 under the following exemplary conditions. On a benchtop, an 8 mL vial equipped with a magnetic stir-bar an be charged with: 50 mg of first polyurethane 702 at 0.120 mmol perfluorobenzyl groups); 5.4 mg of sodium dodecanoate at 20 mol % catalyst loading per perfluorobenzyl group; and 0.050 mL of DMF. The reaction mixture can be stirred until all of the solids are dissolved. Also, 40 mg of trimethylsilyl protected dodecanethiol at 0.144 mmol, 1.2 equivalent per perfluorobenzyl unit can be added and the reaction mixture can be stirred at RT for 5 min. An aliquot can be removed and analyzed by F NMR to determine conversion (e.g., >95%). The remainder of reaction mixture can be purified by dialysis (e.g., 20% water in MeOH for 24 hours with the solvent changed twice).

Figure 12:
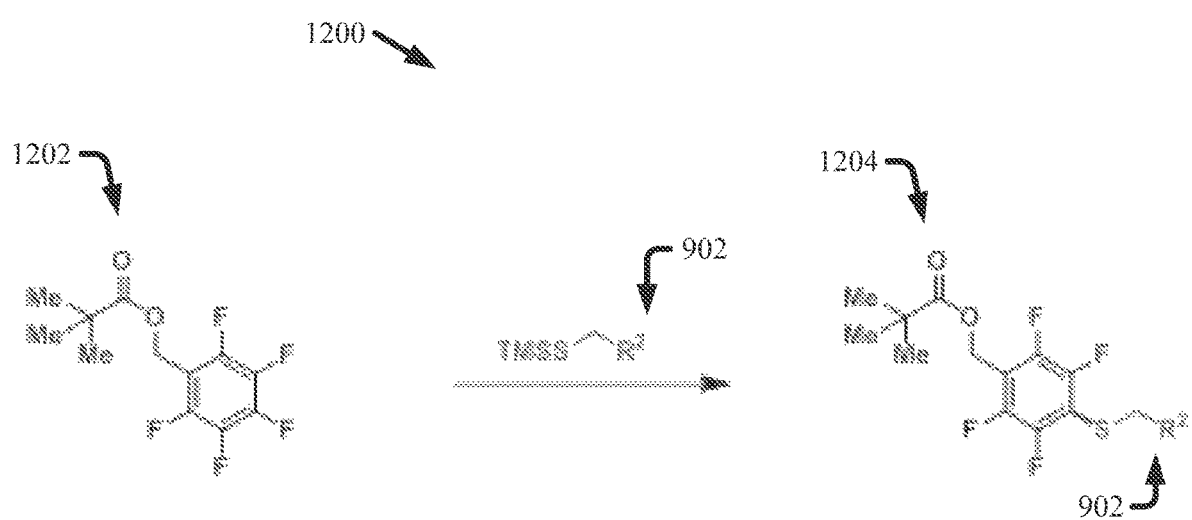
FIG. 12 illustrates a diagram of an example, non-limiting functionalization scheme that can facilitate post-synthesis functionalization of one or more chemical compounds in accordance with one or more embodiments described herein.

FIG. 12 illustrates a diagram of an example, non-limiting functionalization scheme 1200 that can facilitate functionalizing one or more chemical compounds (e.g., that can comprise one or more pendent functional groups 104), that can be a polymer and/or monomer, in accordance with one or more embodiments described herein (e.g., method 800). Repetitive description of like elements employed in other embodiments described herein is omitted for sake of brevity. While one or more particular reactants (e.g., monomer reactant 1202) are depicted; additional embodiments of functionalization scheme 1200 are also envisaged. For example, the principal mechanisms of functionalization scheme 1200 can be applied to other reactants (e.g., other monomers comprising a pendent functional group 104) in accordance with the various features described herein. Reactants that can be functionalized in accordance with functionalization scheme 1200 can include monomers and/or polymers that can comprise a molecular backbone bonded to one or more pendent functional groups 104, wherein the molecular backbone can comprise: one or more carbonate structures, one or more urethane structures, one or more amide structures, one or more ester structures, one or more ether structures, one or more acrylate structures, and/or one or more styrene structures.

Functionalization scheme 1200 can depict a functionalization of one or more monomers that can comprise one or more pendent functional groups 104 (e.g., monomer reactant 1202) with one or more trimethylsilyl protected thiols (represented by "TMSS" in FIG. 12), which can comprise one or more second functional group 902 (e.g., represented by "R²" in FIG. 12), to form a functionalized monomer (e.g., first functionalized monomer 1204). Functionalization scheme 1200 can generate mono-substituted functionalized monomers (e.g., first functionalized monomer 1204) and/or poly-substituted functionalized monomers.

The one or more second functional groups 902 can comprise: alkyl structures, aryl structures, carboxyl groups, carbonyl groups, amine groups, amide groups, ether groups, ester groups, ketone groups, hydroxyl groups, alkenyl groups, aldehyde groups, alkene groups, a combination thereof, and/or the like. For example, the one or more second functional groups 902 can be undecane, thereby the one or more trimethylsilyl protected thiols can be trimethylsilyl protected dodecanethiol.

To facilitate functionalization, the one or more monomer reactants that can comprise one or more pendent functional groups 104 (e.g., monomer reactant 1202), the one or more trimethylsilyl protected thiols, and/or a catalyst can be dissolved in a solvent to form a mixture. The solvent can be organic and/or polar. Example solvents include, but are not limited to DMF, NMP, a combination thereof, and/or the like. To facilitate functionalization, the mixture can be stirred at a temperate greater than or equal to 10° C. and less than or equal to 150° C. (e.g., RT) for a period of time greater than or equal to 2 minutes and less than or equal to 48 hours (e.g., 5 minutes).

Table 2, presented below, regards functionalization of monomer reactant 1202 in accordance with functionalization scheme 1200 with a variety of catalysts.

TABLE 2

| Entry | Catalyst | Mol % | Conversion (%) |
|---|---|---|---|
| 1 | None | — | 6 |
| 2 | DBU•PhCO₂H | 20 | >95 |
| 3 | Potassium Acetate | 20 | >95 |
| 4 | Sodium Trifluoromethanesulfonate | 20 | 9 |
| 5 | Sodium Trifluoroacetic Acid | 20 | 12 |
| 6 | Lithium 2-ethylhexanoate | 20 | >95 |

Additionally, experiments utilizing pyridinium p-toluenesulfonate as a catalyst resulted in zero conversion. In various embodiments, the catalysts of Table 2 are also applicable with method 800, the functionalization schemes of FIG. 9, and/or functionalization scheme 1200.

Figure 13:
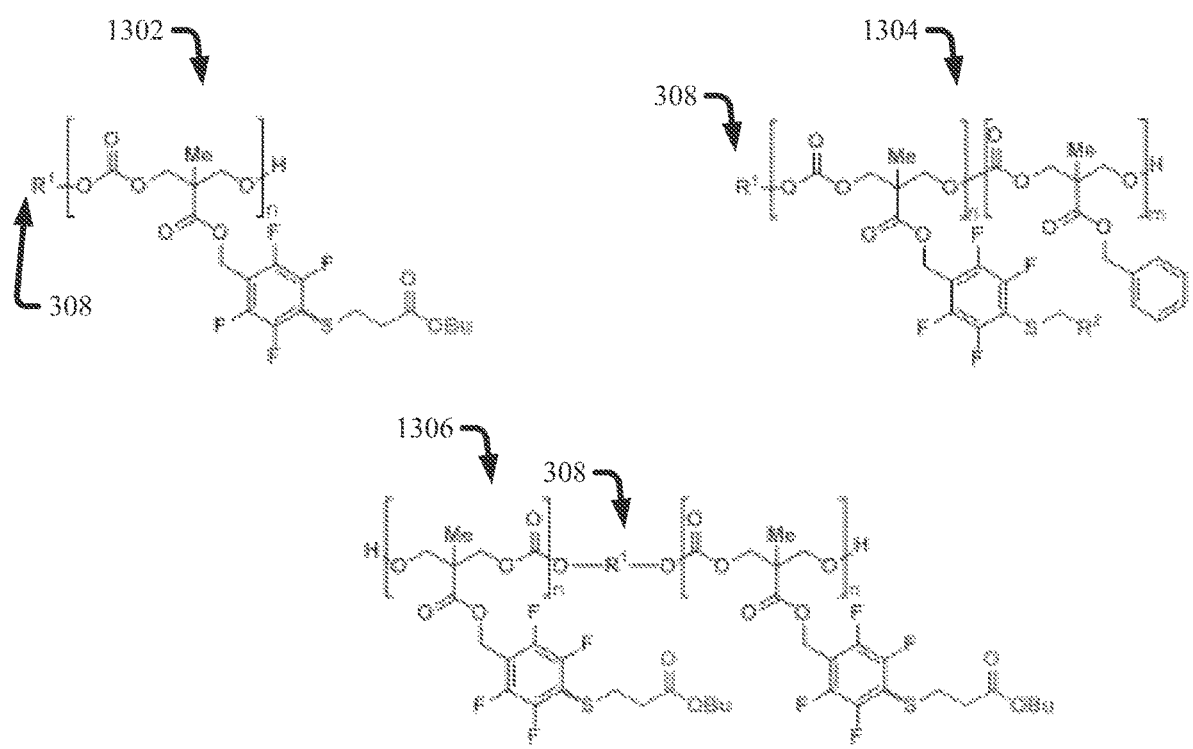
FIG. 13 illustrates a diagram of example, non-limiting chemical compounds that can be generated by post-synthesis functionalization in accordance with one or more embodiments described herein.

FIG. 13 illustrates a diagram of example, non-limiting functionalized polycarbonates that can be generated in accordance with method 800 and/or the functionalization schemes shown in FIG. 9. Repetitive description of like elements employed in other embodiments described herein is omitted for sake of brevity. For example, eighth polycarbonate 1302 can be an embodiment of fourth polycarbonate 904. Also, ninth polycarbonate 1304 can be generated from second polycarbonate 404 in accordance with method 800 and/or the functionalization schemes shown in FIG. 9. Additionally, tenth polycarbonate 1306 can be generated from third polycarbonate 406 in accordance with method 800 and/or the functionalization schemes shown in FIG. 9. Thus, it is evident from the examples shown in FIG. 13 that the functionalizing described herein (e.g., with reference to method 800, the functionalization schemes of FIG. 9, and/or functionalization scheme 1100) can be performed on polymers (e.g., homopolymers) and/or copolymers (e.g., alternating copolymers, random copolymers, and/or block copolymers).

Figure 14:
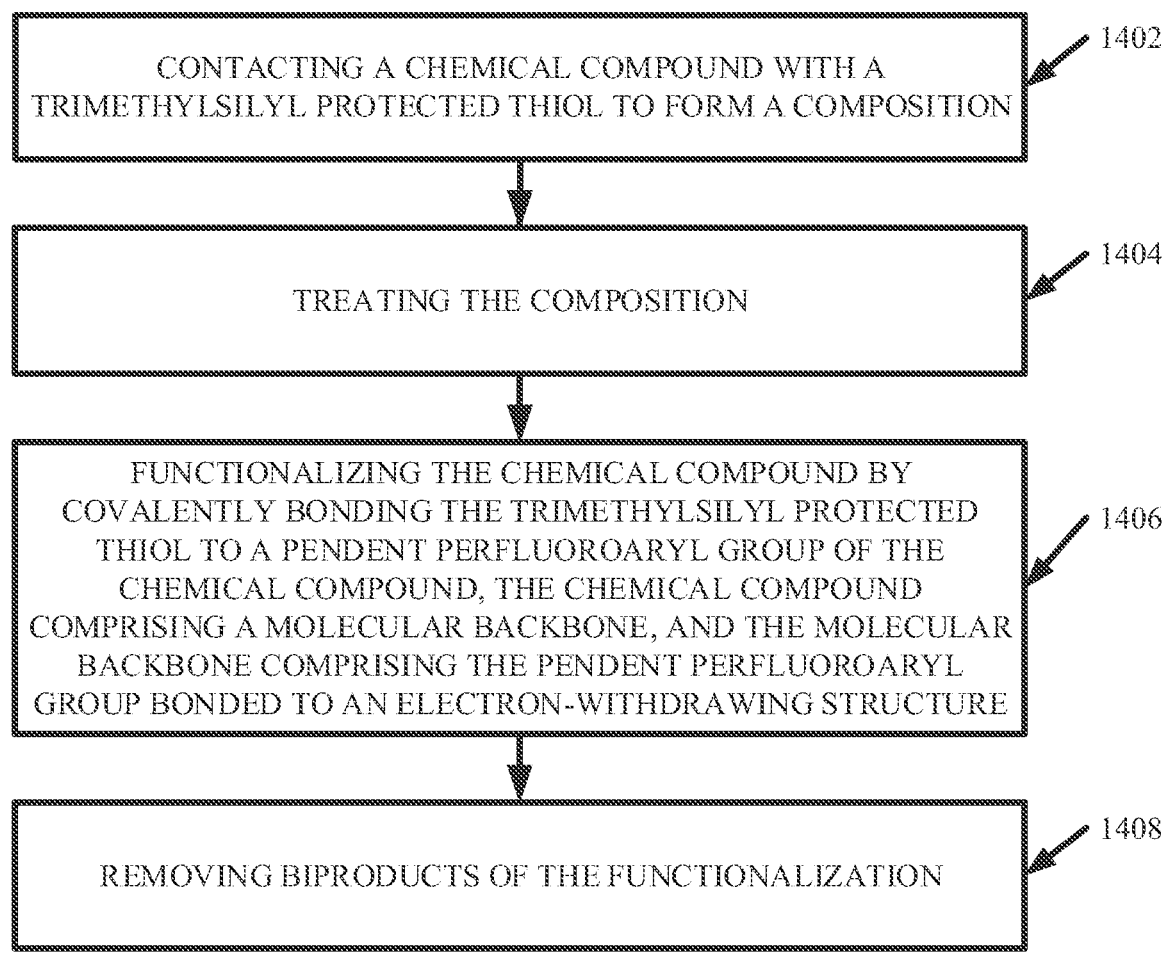
FIG. 14 illustrates a flow diagram of an example, non-limiting method that can facilitate surface functionalization of one or more chemical compounds in accordance with one or more embodiments described herein.

FIG. 14 illustrates a flow diagram of an example, non-limiting method 1400 that can facilitate surface functionalization of one or more chemical compounds in accordance with one or more embodiments described herein. Repetitive description of like elements employed in other embodiments described herein is omitted for sake of brevity. In various embodiments, method 1400 can be utilized to functionalize perfluoroaryl coated surfaces.

At 1402, the method 1400 can comprise contacting a chemical compound with one or more trimethylsilyl protected thiols to form a composition. The chemical compound can comprise one or more monomers and/or one or more polymers (e.g., homopolymers, alternating copolymers, random copolymers, and/or block copolymers). For example, the chemical compound can be located on a surface of an article and the contacting can comprise dispersing (e.g., spraying and/or coating) the chemical compound covered surface with the one or more trimethylsilyl protected thiols.

At 1404, the method 1400 can comprise treating the composition to facilitate functionalizing the compound. The treating can comprise one or more heat treatments and/or one or more chemical treatments. For example, the composition can be heated to a curing temperature (e.g., a temperature greater than or equal to 150° C. and less than or equal to 300° C.).

At 1406, the method 1400 can comprise functionalizing the chemical compound by covalently bonding the one or more trimethylsilyl protected thiols to a pendent perfluoroaryl group of the chemical compound. The chemical compound can comprise a molecular backbone comprising one or more pendent perfluoroaryl groups covalently bonded to one or more electron-withdrawing structures. For example, the one or more pendent perfluoroaryl groups can be pendent perfluorophenyl groups. The functionalizing at 1406 can generate mono-substituted products and/or poly-substituted products. The low surface energy of fluorine can enable preferential orientation of the one or more perfluoroaryl groups away from a surface, making the chemical compound more accessible for substitution by nucleophiles.

Unlike the pendent functional groups 104 that can comprise chemical compounds that can be characterized by chemical formula 100, 300, and/or 302, which bond a perfluoroaryl group to a molecular backbone and/or linkage group 306 via a methylene group; the chemical compound of method 1400 can comprise one or more pendent perfluoroaryl groups bonded directly to a molecular backbone without one or more intermediate methylene groups. Additionally, the one or more pendent perfluoroaryl groups can be bonded directly to one or more electron-withdrawing structures. Example electron-withdrawing structures can include, but are not limited to, amide structures and/or sulphonamide structures. Thus, the one or more pendent perfluoroaryl groups can be electron deficient.

At 1408, the method 1400 can optionally comprise removing biproducts of the functionalization at 1406. For example, the surface can be rinsed and/or otherwise washed to remove salt biproducts, thereby rendering a functionalized surface free of contaminants.

Figure 15:
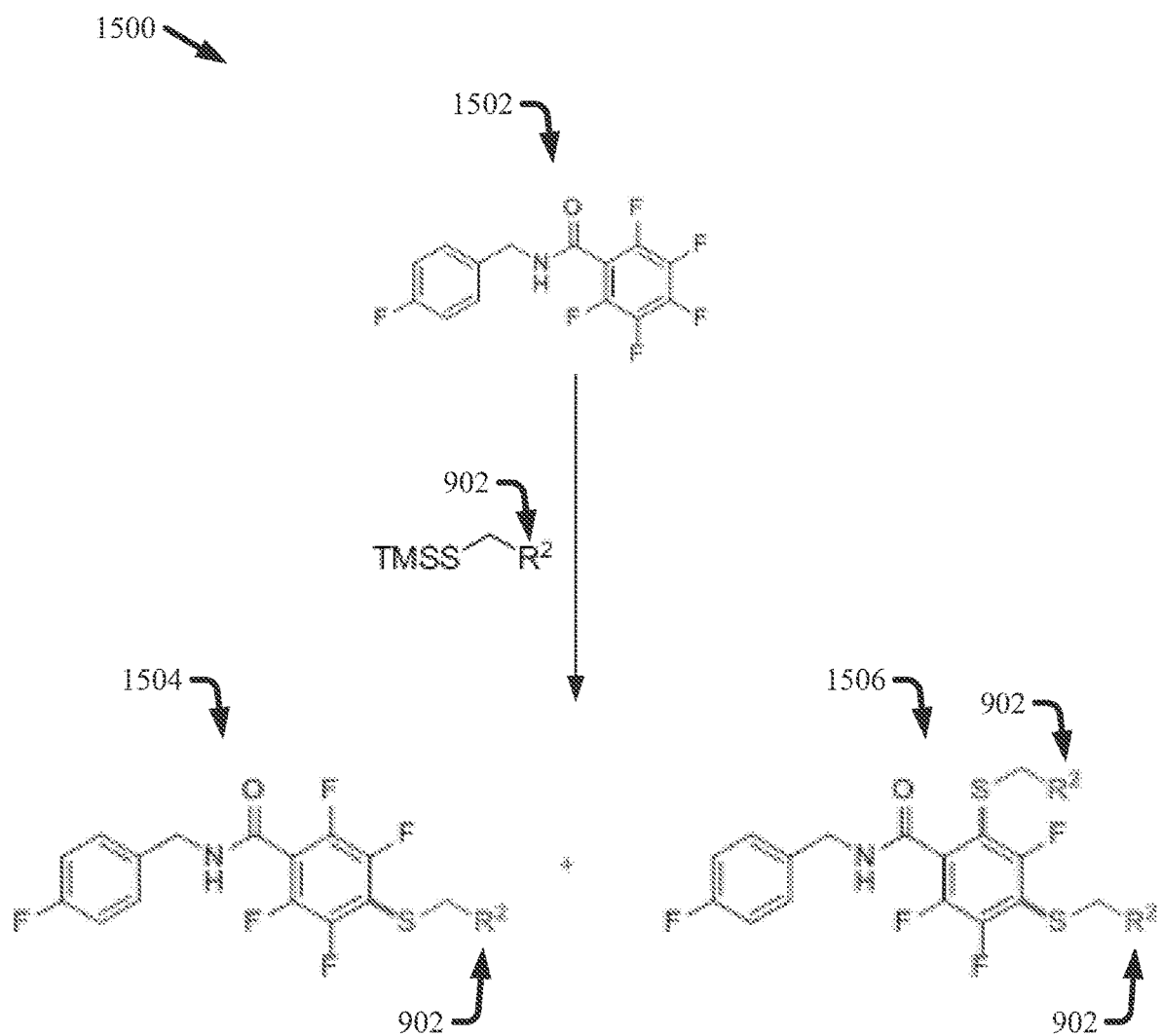
FIG. 15 illustrates a flow diagram of an example, non-limiting surface functionalization scheme that can facilitate post-synthesis functionalization of one or more chemical compounds in accordance with one or more embodiments described herein.

FIG. 15 illustrates a diagram of an example, non-limiting functionalization scheme 1500 that can facilitate functionalizing one or more chemical compound in accordance with one or more embodiments described herein (e.g., method 1400). Repetitive description of like elements employed in other embodiments described herein is omitted for sake of brevity. While one or more particular reactants (e.g., reactant 1502) are depicted; additional embodiments of functionalization scheme 1500 are also envisaged. For example, the principal mechanisms of functionalization scheme 1500 can be applied to other reactants (e.g., other chemical compounds comprising a pendent perfluoroaryl group bonded to an electron-withdrawing structure) in accordance with the various features described herein.

Functionalization scheme 1500 can facilitate generating one or more functionalized chemical compounds in accordance with method 1400. For example, the functionalization can comprise functionalizing one or more perfluoroaryl groups of one or more chemical compounds with one or more trimethylsilyl thiols (e.g., represented by "TMSS" in FIG. 15). The one or more perfluoroaryl groups (e.g., perfluorophenyl groups) can be directly bonded to one or more electron-withdrawing structures (e.g., comprising an amide group and/or a sulphonamide group), thereby rendering the one or more perfluoroaryl groups electron deficient. The one or more trimethylsilyl thiols can comprise one or more second functional group 902 (e.g., represented by "R²" in FIG. 15). The second functional group 902 can comprise: alkyl structures, aryl structures, carboxyl groups, carbonyl groups, amine groups, amide groups, ether groups, ester groups, ketone groups, hydroxyl groups, alkenyl groups, aldehyde groups, alkene groups, a combination thereof, and/or the like. For example, the one or more second functional groups 902 can be undecane, thereby the one or more trimethylsilyl protected thiols can be trimethylsilyl protected dodecanethiol.

The functionalization depicted by functionalization scheme 1500 can be catalyst-free. Additionally, the functionalization can generate mono-substituted functionalized chemical compounds (e.g., first functionalized compound 1504) and/or poly-substituted functionalized chemical compounds (e.g., second functionalized compound 1506). Moreover, the functionalization depicted by functionalization scheme 1500 can be: facilitated by a solvent (e.g., NMP); performed at a temperature greater than or equal to 10° C. and less than or equal to 150° C. (e.g., RT); and can comprise a reaction duration greater than or equal to 2 minutes and less than or equal to 48 hours (e.g., 18 hours).

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, compositions, and methods. It is, of course, not possible to describe every conceivable combination of reagents, products, solvents, and/or articles for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A chemical compound comprising:
   a molecular backbone comprising a plurality of urethane groups; and
   a pendent functional group covalently bonded to an amine group of at least one of the plurality of urethane groups via a methylene group, the pendent functional group comprising a perfluoroaryl group.

2. The chemical compound of claim 1, wherein the molecular backbone further comprises a carbamate group.

3. The chemical compound of claim 1, wherein the pendent functional group is a perfluorobenzyl group.

4. The chemical compound of claim 2, wherein the carbamate group is derived from an isocyanate.

5. A polymer comprising:
   a molecular backbone comprising a polyurethane structure; and
   a pendent functional group covalently bonded to an amino group of the molecular backbone via a methylene group, the pendent functional group comprising a perfluoroaryl group and a methylene group.

6. The polymer of claim 5, wherein the molecular backbone further comprises a carbamate group.

7. The polymer of claim 5, wherein the polymer is characterized by a chemical formula:

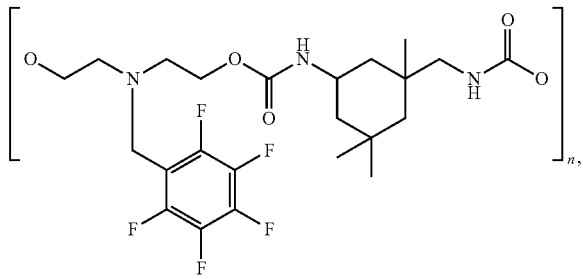

wherein n is an integer greater than or equal to two and less than or equal to one thousand.

8. The polymer of claim 6, wherein the pendent functional group is a perfluorobenzyl group.

9. The polymer of claim 8, wherein the carbamate group is derived from an isocyanate.

10. The polymer of claim 5, wherein the polymer is characterized by a chemical formula:

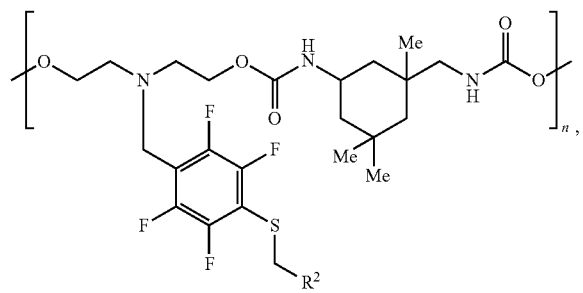

wherein n is an integer greater than or equal to two and less than or equal to one thousand, and wherein $R^2$ comprises one or more functional groups.

11. The polymer of claim 10, wherein $R^2$ comprises a functional group selected from the group consisting of: an alkyl structure, an aryl structure, a carboxyl group, a carbonyl group, an amine group, an amide group, an ether group, an ester group, a ketone group, a hydroxyl group, an alkenyl group, an aldehyde group, and an alkene group.

12. The polymer of claim 10, wherein $R^2$ comprises undecane.

13. The chemical compound of claim 1, wherein the pendent functional group comprises the methylene group.

14. The chemical compound of claim 1, wherein the chemical compound is characterized by a chemical formula:

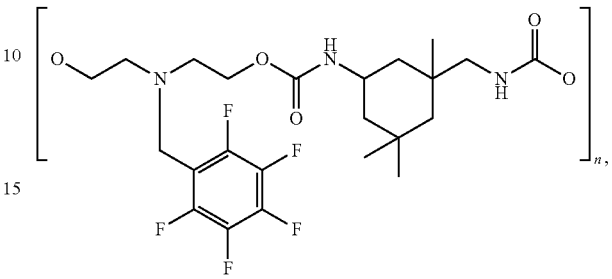

wherein n is an integer greater than or equal to two and less than or equal to one thousand.

15. The chemical compound of claim 1, wherein the chemical compound is characterized by a chemical formula:

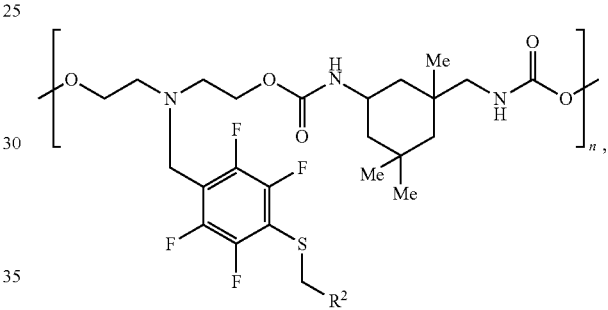

wherein n is an integer greater than or equal to two and less than or equal to one thousand, and wherein $R^2$ comprises one or more functional groups.

16. The chemical compound of claim 15, wherein $R^2$ comprises a functional group selected from the group consisting of: an alkyl structure, an aryl structure, a carboxyl group, a carbonyl group, an amine group, an amide group, an ether group, an ester group, a ketone group, a hydroxyl group, an alkenyl group, an aldehyde group, and an alkene group.

17. The chemical compound of claim 15, wherein $R^2$ comprises undecane.

* * * * *